US012582314B2

(12) United States Patent
Tseng et al.

(10) Patent No.: US 12,582,314 B2
(45) Date of Patent: Mar. 24, 2026

(54) SENSING DEVICE

(71) Applicant: Advanced Semiconductor Engineering, Inc., Kaohsiung (TW)

(72) Inventors: Kuei-Hao Tseng, Kaohsiung (TW); Kai Hung Wang, Kaohsiung (TW); Kai-Di Lu, Kaohsiung (TW); Yu-Chih Lee, Kaohsiung (TW); Cheng-Tsao Peng, Kaohsiung (TW); Pang Yuan Lee, Kaohsiung (TW)

(73) Assignee: Advanced Semiconductor Engineering, Inc., Kaohsiung (TW)

( * ) Notice: Subject to any disclaimer, the term of this patent is extended or adjusted under 35 U.S.C. 154(b) by 495 days.

(21) Appl. No.: 18/083,447

(22) Filed: Dec. 16, 2022

(65) Prior Publication Data

US 2024/0197176 A1 Jun. 20, 2024

(51) Int. Cl.
*A61B 5/00* (2006.01)
*H05K 1/02* (2006.01)

(52) U.S. Cl.
CPC ......... *A61B 5/0002* (2013.01); *H05K 1/0277* (2013.01)

(58) Field of Classification Search
None
See application file for complete search history.

(56) References Cited

U.S. PATENT DOCUMENTS

| | | | | |
|---|---|---|---|---|
| 7,230,321 B2 * | 6/2007 | McCain | ................. | H01L 23/58 |
| | | | | 438/111 |
| 9,455,230 B1 * | 9/2016 | Park | ................. | H01L 23/49827 |
| 10,083,911 B2 * | 9/2018 | Hsieh | .................... | H01L 21/561 |
| 10,201,703 B2 * | 2/2019 | Bogie | ................ | A61N 1/36031 |
| 11,020,008 B2 * | 6/2021 | Coulon | .................. | A61B 5/366 |
| 12,245,872 B2 * | 3/2025 | Lin | ....................... | A61B 5/7225 |
| 2016/0287868 A1 * | 10/2016 | Bogie | ................ | A61N 1/36031 |
| 2018/0226348 A1 * | 8/2018 | Hsieh | .................. | H01L 23/3121 |
| 2018/0333058 A1 * | 11/2018 | Coulon | .................. | A61B 5/318 |
| 2018/0369582 A9 * | 12/2018 | Bogie | ................ | A61N 1/36031 |
| 2020/0171495 A1 * | 6/2020 | Jones | ................ | B01L 3/502715 |
| 2022/0117503 A1 * | 4/2022 | Wang | ................. | A61B 5/14521 |
| 2022/0346715 A1 | 11/2022 | Lin et al. | | |
| 2023/0157607 A1 * | 5/2023 | Guermonprez | .......... | A61B 5/27 |
| | | | | 600/379 |
| 2023/0282962 A1 * | 9/2023 | Wei | ........................ | H01Q 1/273 |
| | | | | 343/700 R |
| 2025/0064359 A1 * | 2/2025 | Adler | ................. | A61B 5/14865 |

* cited by examiner

*Primary Examiner* — Shirley X Jian
(74) *Attorney, Agent, or Firm* — Foley & Lardner LLP

(57) ABSTRACT

The present disclosure provides a sensing device. The sensing device includes a flexible element having a first sensing area, an electronic component embedded within the flexible element, and an adjustable conductive element disposed in the flexible element and configured to electrically connect the first sensing area of the flexible element with the electronic component.

20 Claims, 20 Drawing Sheets

1a

SENSING DEVICE

BACKGROUND

1. Technical Field

The present disclosure relates to a sensing device.

2. Description of the Related Art

Sensing devices may be integrated into wearable devices to obtain signals or information reflecting physical activity and/or health. Conventionally, signals or pieces of information detected or collected by the sensing devices are transmitted to processing devices through conductive elements (e.g., wires, cables, circuit layers, etc.). Noise and interference problems exist and become severe with long transmission paths between the sensing devices and the processing devices, affecting transmission properties and sensing quality.

SUMMARY

In some arrangements, a sensing device includes a flexible element having a first sensing area, an electronic component embedded within the flexible element, and an adjustable conductive element disposed in the flexible element and configured to electrically connect the first sensing area of the flexible element with the electronic component.

In some arrangements, a sensing device includes a carrier having a surface, an electronic component disposed over the surface of the carrier, and an adjustable conductive element having at least two opposite ends connecting to the surface of the carrier. The adjustable conductive element is electrically connected with the electronic component through the carrier and configured to transmit a biological signal to the electronic component.

In some arrangements, a sensing device includes a conductive flexible element configured to collect a biological signal, a non-conductive flexible element bonded with the conductive flexible element, and an adjustable conductive element configured to increase a bonding strength between the conductive flexible element and the non-conductive flexible element.

BRIEF DESCRIPTION OF THE DRAWINGS

Aspects of some arrangements of the present disclosure are best understood from the following detailed description when read with the accompanying figures. It is noted that various structures may not be drawn to scale, and dimensions of the various structures may be arbitrarily increased or reduced for clarity of discussion.

FIG. 1D-2 illustrates a cross-sectional view of a sensing device in accordance with some arrangements of the present disclosure.

FIG. 1I-1 illustrates a cross-sectional view of a sensing device in accordance with some arrangements of the present disclosure.

FIG. 1I-2 illustrates a cross-sectional view of a sensing device in accordance with some arrangements of the present disclosure.

DETAILED DESCRIPTION

Figure 1A:
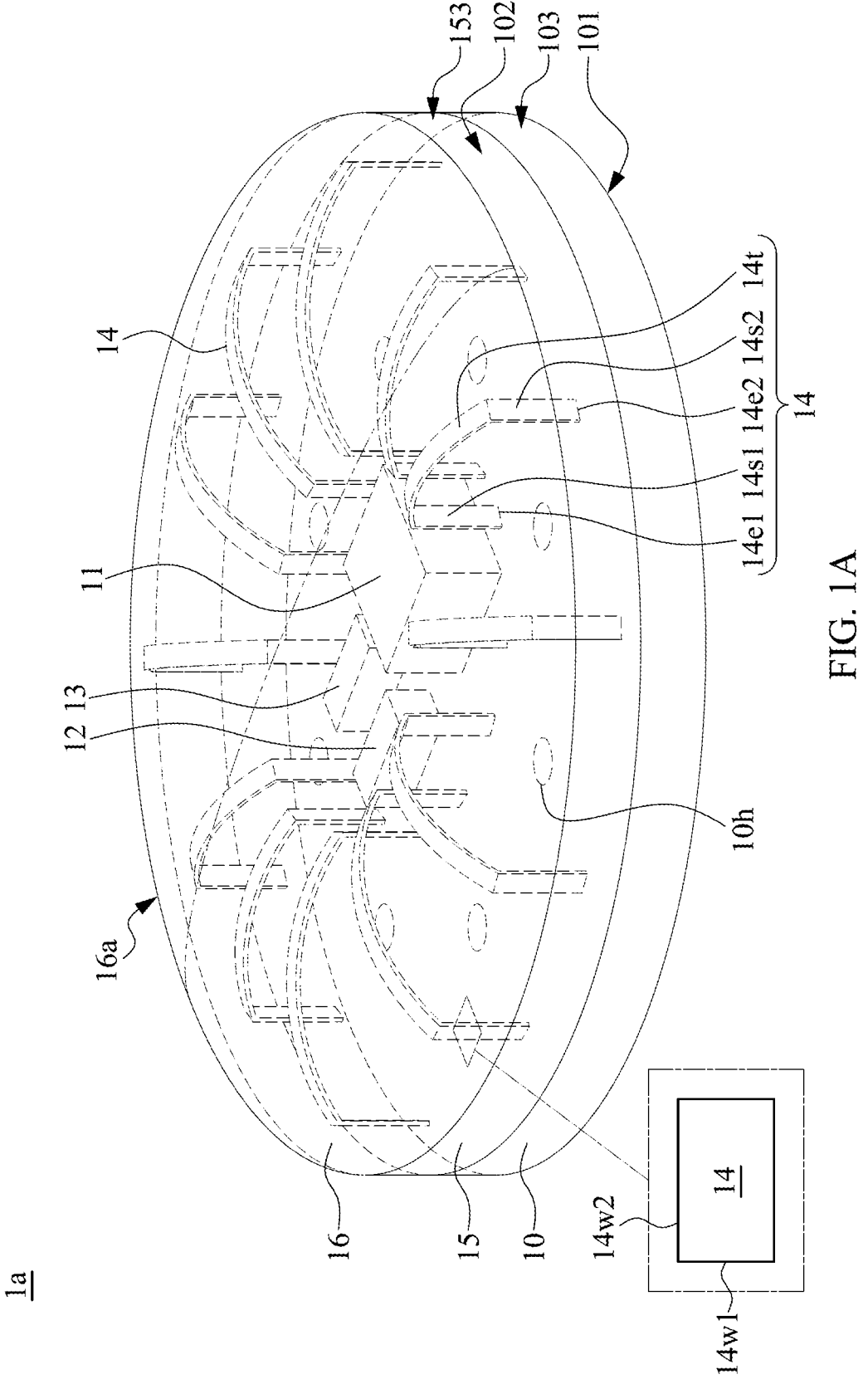
FIG. 1A illustrates a perspective view of a sensing device in accordance with some arrangements of the present disclosure.

The following disclosure provides for many different arrangements, or examples, for implementing different features of the provided subject matter. Specific examples of components and arrangements are described as follows to explain certain aspects of the present disclosure. These are, of course, merely examples and are not intended to be limiting. For example, the formation of a first feature over or on a second feature in the description that follows may include arrangements in which the first and second features are formed or disposed in direct contact, and may also include arrangements in which additional features may be formed or disposed between the first and second features, such that the first and second features may not be in direct contact. In addition, the present disclosure may repeat reference numerals and/or letters in the various examples. This repetition is for the purpose of simplicity and clarity and does not in itself dictate a relationship between the various arrangements and/or configurations discussed.

Spatial descriptions, such as "above," "below," "up," "left," "right," "down," "top," "bottom," "vertical," "horizontal," "side," "higher," "lower," "upper," "over," "under," and so forth, are indicated with respect to the orientation shown in the figures unless otherwise specified. It should be understood that the spatial descriptions used herein are for purposes of illustration only, and that practical implementations of the structures described herein can be spatially arranged in any orientation or manner, provided that the merits of arrangements of this disclosure are not deviated from by such arrangement.

Figure 1B:
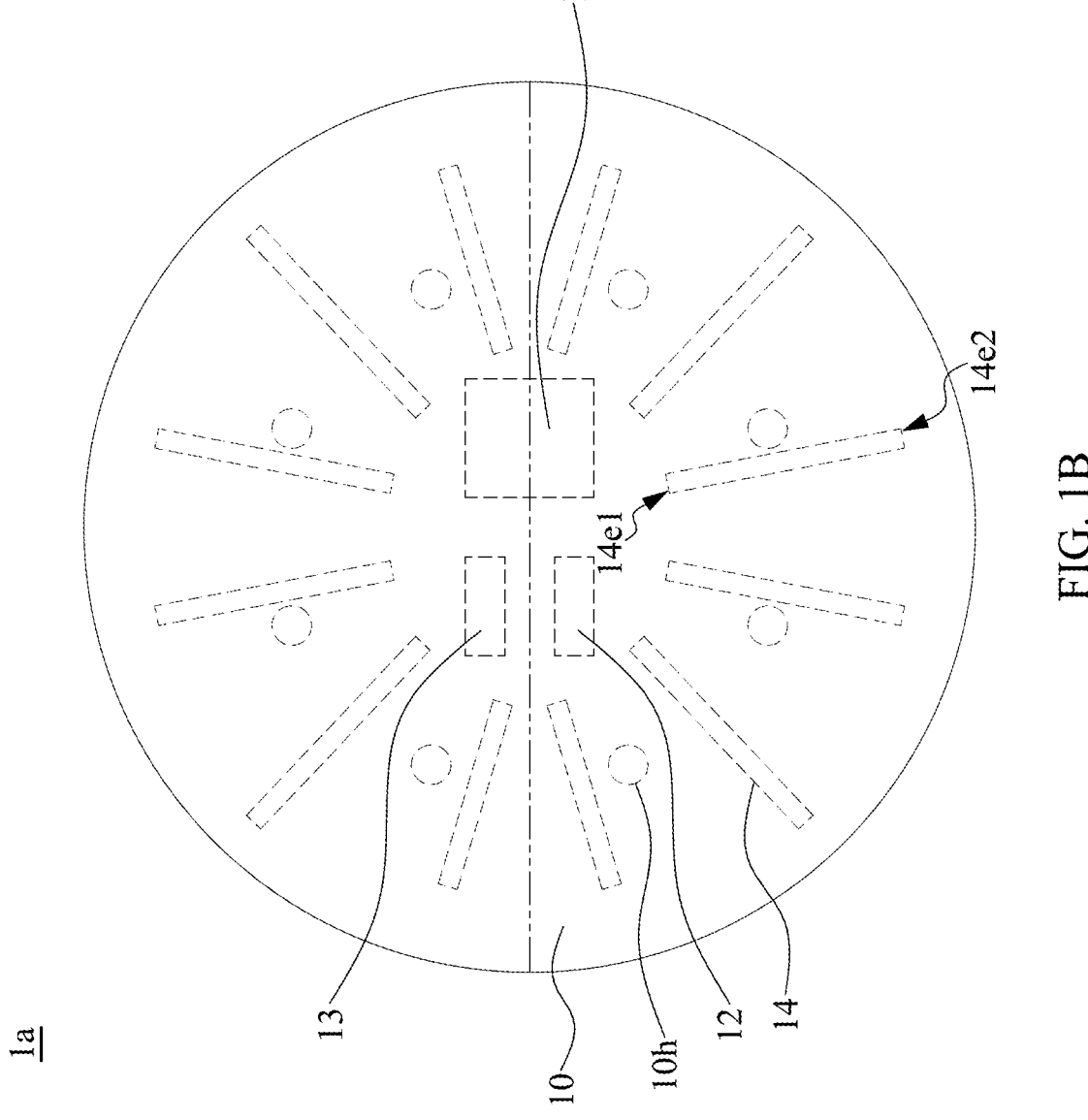
FIG. 1B illustrates a top view of a sensing device in accordance with some arrangements of the present disclosure.
Figure 1C:
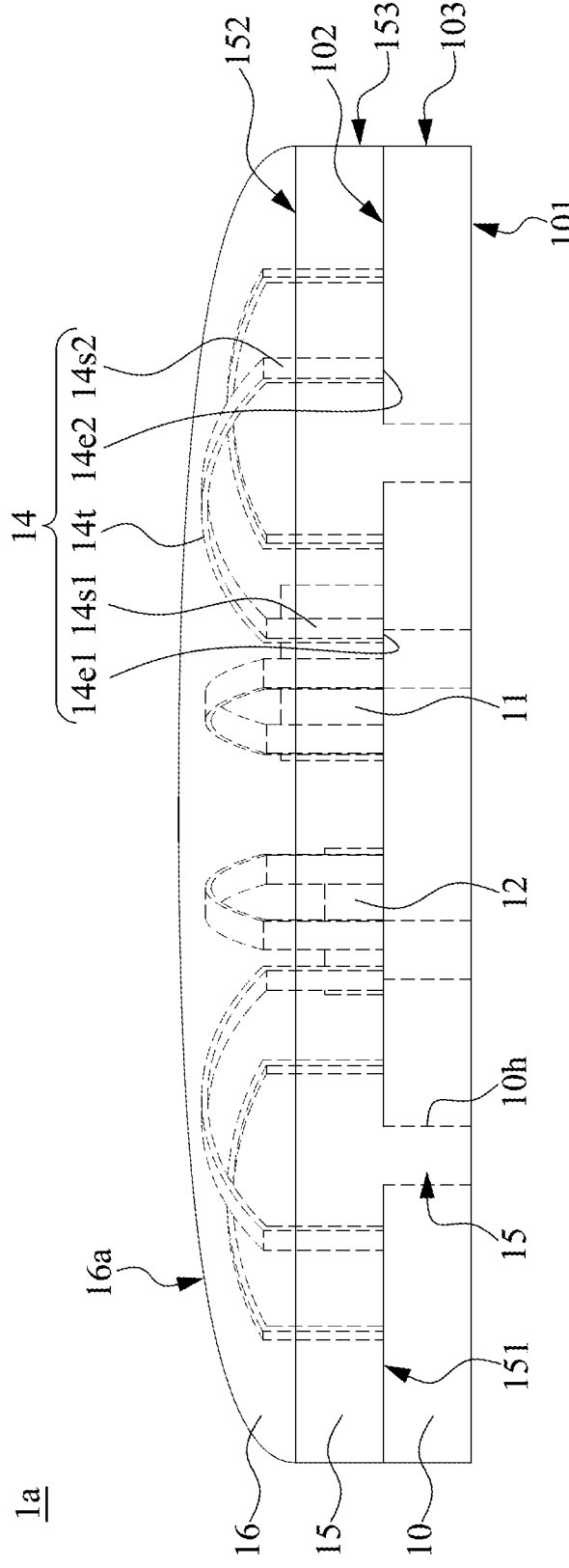
FIG. 1C illustrates a side view of a sensing device in accordance with some arrangements of the present disclosure.

FIG. 1A illustrates a perspective view of a sensing device 1a in accordance with some arrangements of the present disclosure. FIG. 1B and FIG. 1C illustrate a top view and a side view, respectively, of the sensing device 1a in accordance with some arrangements of the present disclosure.

In some arrangements, the sensing device 1a may include or be a part of an electronic device package or an electronic device module, such as a system-in-package (SiP) module. In some arrangements, the sensing device 1a may include or be a part of a wearable device. For example, the sensing device 1a may be configured to be worn by and/or attached to an object or a target. The object (or a wearing object) may include a human or an animal.

The sensing device 1a may also be referred to as a monitoring device or a detecting device. In some arrangements, the sensing device 1a may be a piece of equipment that detects signals or pieces of information, such as biological signals, physiological signals, motions (e.g., body motions of the human or animal), and/or environmental information in a vicinity of an object.

Configuration or application of the sensing device 1a in the figures is for illustrative purposes only, and not intended to limit the present disclosure. Exemplary sensing devices may be embodied in an earpiece, a headpiece, a finger clip, a digit (finger or toe) piece, a watch, a limb band (such as an arm band or leg band), an ankle band, a wrist band, a nose piece, a sensor patch, eyewear (such as glasses or shades), apparel (such as a shirt, hat, underwear, etc.), a mouthpiece or tooth piece, contact lenses, or the like.

Referring to FIGS. 1A, 1B, and 1C, the sensing device 1a may include a carrier 10, electronic components 11, 12, 13, one or more flexible connection elements 14, and encapsulants 15, 16.

The carrier 10 may include a substrate. The carrier 10 may include a printed circuit board (PCB), such as a paper-based copper foil laminate, a composite copper foil laminate, or a polymer-impregnated glass-fiber-based copper foil laminate. In some arrangements, the substrate 10 may include an interconnection structure, such as a redistribution layer (RDL) or a grounding element.

The carrier 10 may include a surface 101, a surface 102 opposite to the surface 101, and a surface (or a lateral surface) 103 extending between the surface 101 and the surface 102. The carrier 10 may include one or more conductive pads (not shown) in proximity to, adjacent to, or embedded in and exposed from the surface 101 and/or 102 of the carrier 10. The carrier 10 may include a solder resist (not shown) on the surface 101 and/or 102 of the carrier 10 to fully expose or to expose at least a portion of the conductive pads for electrical connections.

The carrier 10 may include one or more holes or vias 10h. The holes 10h may form a circle from the top view. However, in some arrangements, the holes 10h may form an oval, a square, a rectangle, a triangle, or other shapes. The holes 10h may be equally spaced from the top view. For example, the holes 10h may be arranged over the surface 102 of the carrier 10 by an equal spacing or interval. However, in some arrangements, the holes 10h may be arranged over the surface 102 of the carrier 10 randomly.

The holes 10h may at least partially penetrate the carrier 10. For example, the holes 10h may extend between the surface 101 and the surface 102. However, in some arrangements, the holes 10h may include blind via holes. For example, the holes 10h may have bottoms at an elevation between the surface 101 and the surface 102.

The holes 10h may include inner through holes and may not be exposed from the surface 103. The holes 10h may each include a constant width. However, in some arrangements, one or more of the holes 10h may taper toward the surface 101 or taper toward the surface 102.

The holes 10h may be filled with the encapsulant 15. For example, the encapsulant 15 may be disposed over or on the surface 102 of the carrier 10 and extend into the holes 10h. For example, the encapsulant 15 may contact (such as directly contact) the sidewalls of the holes 10h. For example, the encapsulant 15 may be partially exposed from the surface 101 of the carrier 10. For example, the encapsulant 15 and the surface 101 of the carrier 10 may substantially coplanar.

In some arrangements, the carrier 10 and the encapsulant 15 may include different materials. The holes 10h and the encapsulant 15 may function as lock and key elements or interlocking mechanical features. The holes 10h may be configured to bond, connect, or lock the encapsulant 15 over or on the surface 102 of the carrier 10. Therefore, the adhesion force or a bonding strength between the carrier 10 and the encapsulant 15 may be increased.

The electronic components 11, 12, 13 may each be disposed over or on the surface 102 of the carrier 10. The electronic components 11, 12, 13 may each be electrically connected to one or more other components (such as the flexible connection elements 14) and to the carrier 10 (e.g., to the RDL), and electrical connection may be attained by way of flip-chip bonding (e.g., solder bonding), wire bonding, Cu-to-Cu bonding, or hybrid bonding.

The electronic components 11, 12, 13 may each be a chip or a die including a semiconductor substrate, one or more integrated circuit (IC) devices and one or more overlying interconnection structures therein.

In some arrangements, the electronic components 11, 12, 13 may each include an active component, which may rely on an external power supply to control or modify electrical signals. For example, the electronic components 11, 12, 13 may each include a processor, a controller, a memory, or an input/output (I/O) buffer, etc. For example, the electronic components 11, 12, 13 may each include a central processing unit (CPU), a microprocessor unit (MPU), a graphics processing unit (GPU), a microcontroller unit (MCU), an application-specific integrated circuit (ASIC), a field-programmable gate array (FPGA), or another type of computing element or integrated circuit.

In some arrangements, the electronic components 11, 12, 13 may each include a passive component, which may not require an external power source to function and may not provide electrical gain. For example, the electronic components 11, 12, 13 may each include a resistor, a capacitor, an inductor, a transformer, a diode, a thermistor, a varactor, a transducer, etc.

The positions, functions, and number of the electronic components in the sensing device 1a are not intended to limit the present disclosure. For example, there may be any number of the electronic components in the sensing device 1*a* due to design requirements.

The flexible connection elements 14 may each be disposed over or on the surface 102 of the carrier 10. The flexible connection elements 14 may each include at least two opposite ends 14*e*1 and 14*e*2 electrically connected to one or more other components and to the carrier 10 (e.g., to the RDL), and electrical connection may be attained by way of wire bonding, such as ball bonding and wedge bonding. For example, the flexible connection elements 14 may be electrically connected to at least one of the electronic components 11, 12, and 13 through the carrier 10.

The ends 14*e*1 and 14*e*2 may contact (such as directly contact) the surface 102 of the carrier 10. The flexible connection elements 14 may each include two straight (e.g., vertical) sides or walls 14*s*1 and 14*s*2, and a curved top or bridge 14*t* connecting between the two sides 14*s*1 and 14*s*2. For example, the sides 14*s*1 and 14*s*2 may be perpendicular with respect to the surface 102 of the carrier 10. However, in some arrangements, the flexible connection elements 14 may include conductors of other shapes or configurations, such as wires, wire bundles, cables, pillars, rods, rails, pipes, etc. For example, the sides 14*s*1 and 14*s*2 may be curved. For example, the sides 14*s*1 and 14*s*2 may not be perpendicular with respect to the surface 102 of the carrier 10. The flexible connection elements 14 may each include a bending profile defined by a straight section and a curved section.

In some arrangements, a cross section of one of the flexible connection elements 14 may have different widths 14*w*1 and 14*w*2 in two different dimensions. In some arrangements, a cross section of one of the flexible connection elements 14 may have a rectangular shape.

The flexible connection elements 14 may be configured to be adjustable. In some arrangements, the flexible connection elements 14 may be relatively more resistant to stress, impact, twisting or other physical or structural changes. For example, a flexible connection element 14 may be resilient, such that, after being squeezed or deformed, it can return to its original state.

The flexible connection elements 14 may form a radial pattern from the top view. For example, the ends 14*e*1 of the flexible connection elements 14 may be disposed closer to the central portion of the carrier 10 than the ends 14*e*2 of the flexible connection elements 14. The flexible connection elements 14 may diverge from the central portion of the carrier 10. In some arrangements, the electronic components 11, 12, and 13 may be disposed over the central portion of the carrier 10. However, in some arrangements, the flexible connection elements 14 may be arranged over the surface 102 of the carrier 10 randomly.

The ends 14*e*1 of the flexible connection elements 14 may form a circle from the top view. However, in some arrangements, the ends 14*e*1 of the flexible connection elements 14 may form an oval, a square, a rectangle, a triangle, or other shapes. The ends 14*e*1 of the flexible connection elements 14 may be equally spaced from the top view. For example, the ends 14*e*1 of the flexible connection elements 14 may be arranged over the surface 102 of the carrier 10 by an equal spacing or interval. However, in some arrangements, the ends 14*e*1 of the flexible connection elements 14 may not be equally spaced from the top view.

The positions and number of flexible connection elements 14 in the sensing device 1*a* are not intended to limit the present disclosure. For example, there may be any number of flexible connection elements 14 in the sensing device 1*a* due to design requirements.

The flexible connection elements 14 may each include copper (Cu) or other conductive materials, such as aluminum (Al), chromium (Cr), tin (Sn), gold (Au), silver (Ag), nickel (Ni), stainless steel, another metal, or a mixture, an alloy, or other combinations of two or more thereof.

The encapsulant 15 may be disposed over or on the surface 102 of the carrier 10 to cover or encapsulate the electronic components 11, 12, and 13. The electronic component 11 may be partially covered or encapsulated by the encapsulant 15. The electronic component 11 may be partially exposed from the encapsulant 15.

The electronic components 12 and 13 may be entirely covered or encapsulated by the encapsulant 15. The electronic components 12 and 13 may be embedded in the encapsulant 15.

In some arrangements, the encapsulant 15 may include a surface 151, a surface 152 opposite to the surface 151, and a surface (or a lateral surface) 153 extending between the surface 151 and the surface 152. The surface 151 may face and contact the carrier 10. The surface 152 may face and contact encapsulant 16. The surface 153 may be substantially coplanar or aligned with the surface 103 of the carrier 10.

The encapsulant 16 may be disposed over or on the encapsulant 15. The encapsulant 15 may be disposed between the carrier 10 and the encapsulant 16. The electronic component 11 may be partially covered or encapsulated by the encapsulant 16. The electronic components 12 and 13 may be separated or spaced apart from the encapsulant 16 by the encapsulant 15. The electronic components 12 and 13 may not contact the encapsulant 16.

In some arrangements, the projection areas of the encapsulants 15 and 16 on the carrier 10 may be substantially overlapped. In some arrangements, the projection areas of the encapsulants 15 and 16 on the carrier 10 may be substantially the same. For example, the boundary of the projection area of the encapsulant 15 on the carrier 10 may be substantially aligned with the boundary of the projection area of the encapsulant 16 on the carrier 10.

In some arrangements, the encapsulants 15 and 16 may each include, for example, rubber, silicon, polyester, polyurethane, or other suitable materials such as an elastic material, a soft material, a sponge-like material, or a flexible material. In some arrangements, the encapsulants 15 and 16 may each include a liquid silicone rubber (LSR) or fluoroelastomer (FKM).

In some arrangements, the encapsulants 15 and 16 may each be configured to be adjustable. The encapsulants 15 and 16 may each be soft and flexible enough for the object to be worn comfortably for an extended time period. In some arrangements, the encapsulants 15 and 16 may each be relatively more resistant to stress, impact, twisting or other physical or structural changes. For example, the encapsulants 15 and 16 may each be resilient, such that, after being squeezed or deformed, an encapsulant can return to its original state. In some arrangements, the encapsulants 15 and 16 may each flexibly adjust its shape to conform to the body of the object. In some arrangements, the encapsulants 15 and 16 may be configured to directly contact the body of the object. The encapsulants 15 and 16 may each be biocompatible. For example, the encapsulants 15 and 16 may each not being toxic, injurious, or physiologically reactive and not causing immunological rejection.

In some arrangements, the encapsulants 15 and 16 may have different characteristics or properties. For example, the electrical conductivity of the encapsulant 16 may be higher than the electrical conductivity of the encapsulant 15. For example, the encapsulant 16 may be conductive and the encapsulant 15 may be non-conductive. For example, the encapsulant 16 may include electrically conductive polymers or electrically conductive composite polymers. For example, the encapsulant 16 may include conductive fillers with high conductivity and insulating polymer matrices.

In some arrangements, the electronic components 11, 12, and 13 may be insulated or isolated from the encapsulant 16 by the encapsulant 15. For example, the electronic components 11, 12, and 13 may not be directly electrically connected with the encapsulant 16. For example, the electronic components 11, 12, and 13 may be electrically connected with the encapsulant 16 through the flexible connection elements 14 and the carrier 10.

In some arrangements, the encapsulant 16 may include a sensing area 16a. The sensing area 16a may be configured to contact (such as directly contact) the body of an object. The sensing area 16a may have a curved surface. The sensing area 16a may cover or overlap with the surface area of the carrier 10. For example, the sensing area 16a may extend across the surface area of the carrier 10.

In some arrangements, the encapsulant 16 may be an electrode, a thermistor, a pressure sensor, a proximity sensor, a motion sensor, an acoustic sensor, a smell sensor, a particle sensor, a humidity sensor, an optical transmitter, an optical receiver, an optical transceiver, or a combination thereof. In some arrangements, the encapsulant 16 may be used to detect or collect one or more signals (which may be single-ended signals or differential signals) or pieces of information external to the sensing device 1a.

For example, the encapsulant 16 may be used to detect one or more signals from the surroundings of the sensing device 1a. For example, the encapsulant 16 may be used to detect temperature, air pressure, smell, particle, sound, light, humidity, or other environmental variables.

For example, the encapsulant 16 may be used to detect one or more biological signals or physiological signals of an object. For example, the biological signals detected by the encapsulant 16 may be further processed by the electronic components 11, 12, and 13 to determine a biological parameter of the object, such as a pulse travel time (PTT), an electroencephalogram (EEG), electrocardiogram (ECG), electromyogram (EMG), electrooculogram (EOG), galvanic skin response (GSR), sweat composition, pH, heart rate variability (HRV), or other biologically-relevant information associated with the object. In some arrangements, the electronic components 11, 12, and 13 may be configured to process (e.g., analysis, modify, synthesize, convert to a digital signal, and amplify, etc.), to store, and/or to transmit the detected biological signals.

The flexible connection elements 14 may each be partially covered or encapsulated by the encapsulant 15. The flexible connection elements 14 may each be partially exposed from the encapsulant 15. The flexible connection elements 14 may each be partially covered or encapsulated by the encapsulant 16. Two ends of each of the flexible connection elements 14 may be exposed by the encapsulant 16.

For example, the sides 14s1 and 14s2 of the flexible connection elements 14 may have ends (e.g., the ends 14e1 and 14e2) connecting to the surface 102 of the carrier 10 and extending away from the surface 102 of the carrier 10. The sides 14s1 and 14s2 of the flexible connection elements 14 may extend into the encapsulant 16 and electrically connect to the encapsulant 16. The tops 14t of the flexible connection elements 14 may be at least covered or encapsulated by the encapsulant 16. The tops 14t of the flexible connection elements 14 may contact (such as directly contact) the encapsulant 16. The top 14t of the flexible connection element 14 may be the farthest point or the farthest portion of the flexible connection element 14 from the carrier 10.

In some arrangements, the flexible connection elements 14 may be configured to receive one or more signals or pieces of information from the encapsulant 16 and transmit the signals or pieces of information to the carrier 10. The carrier 10 may further transmit the signals or pieces of information to at least one of the electronic components 11, 12, and 13. The flexible connection elements 14 may provide, constitute, or establish a part of a signal transmission path between the encapsulant 16 and at least one of the electronic components 11, 12, and 13.

In some arrangements, the signals or pieces of information received and transmitted by the flexible connection elements 14 may be different in, for example, signal strength or electrical voltage. In some arrangements, the signals or pieces of information received and transmitted by the flexible connection elements 14 may carry or present different biological or physiological information.

In some comparative arrangements, signals or pieces of information detected or collected by the sensing devices are transmitted to processing devices through conductive elements (e.g., wires, cables, circuit layers, etc.). Noise and interference problems exist and become severe with long transmission paths between the sensing devices and the processing devices, affecting transmission properties and sensing quality.

According to some arrangements, the flexible connection elements 14 may have a relatively lower impedance than the encapsulant 16. For example, the flexible connection elements 14 may be configured to enhance, accelerate, or facilitate the signal transmission between the sensing area 16a of the encapsulant 16 and at least one of the electronic components 11, 12, and 13. For example, the flexible connection elements 14 may be configured to increase the electrical conductivity between the sensing area 16a of the encapsulant 16 and at least one of the electronic components 11, 12, and 13. For example, the flexible connection elements 14 may be configured to increase the signal strength between the sensing area 16a of the encapsulant 16 and at least one of the electronic components 11, 12, and 13. Therefore, the signal noise can be reduced, the problem of transmission loss can be solved, and the sensing quality can be improved.

In addition, incorporating the flexible connection elements 14 into the sensing device 1a can facilitate miniaturization of the sensing device 1a. The overall circuit in the sensing device 1a can consume less power and occupy a smaller area.

Figures 1, 1D:
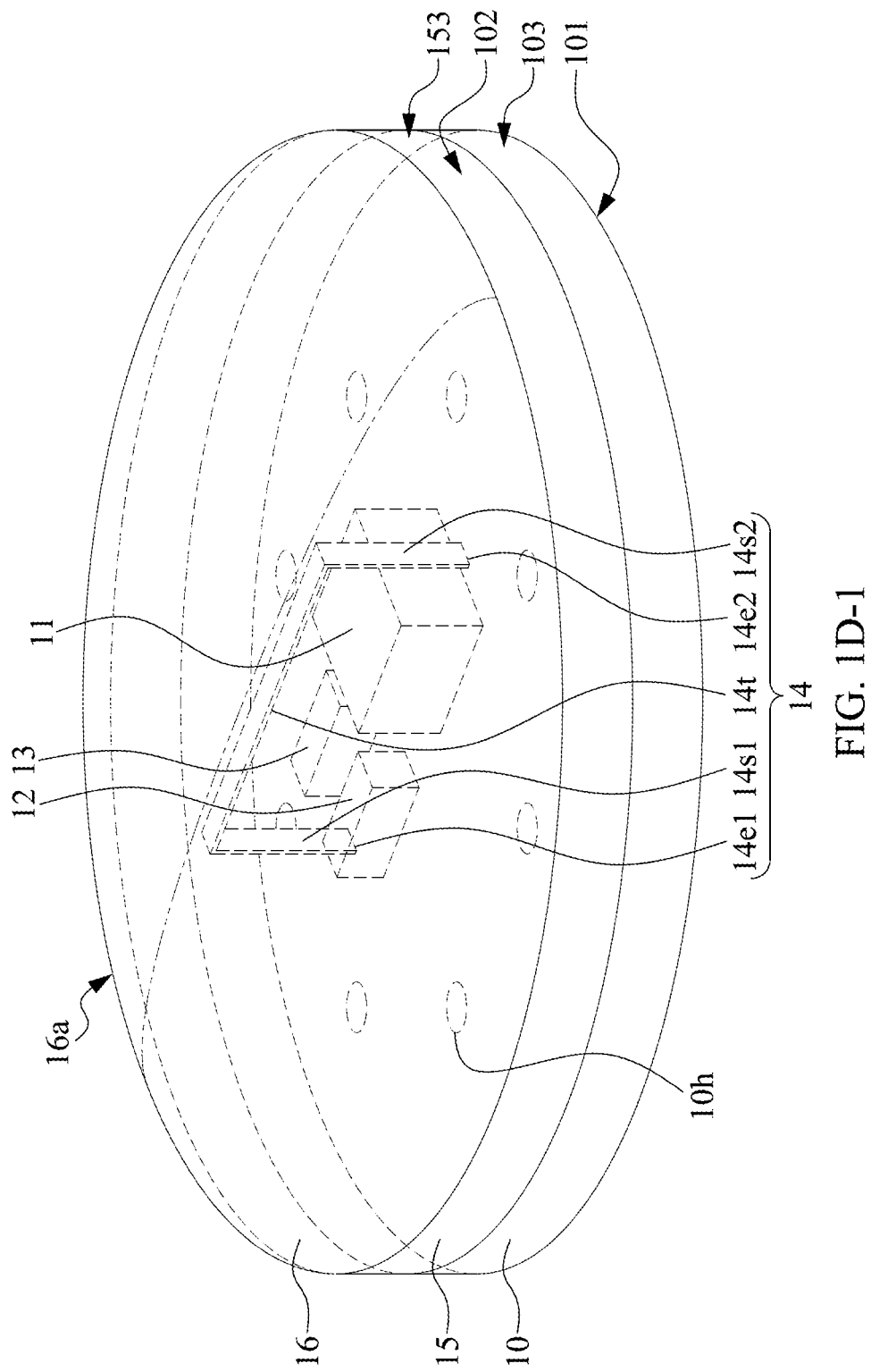
FIG. 1D-1 illustrates a perspective view of a sensing device in accordance with some arrangements of the present disclosure.
Figures 1, 1D, 2:
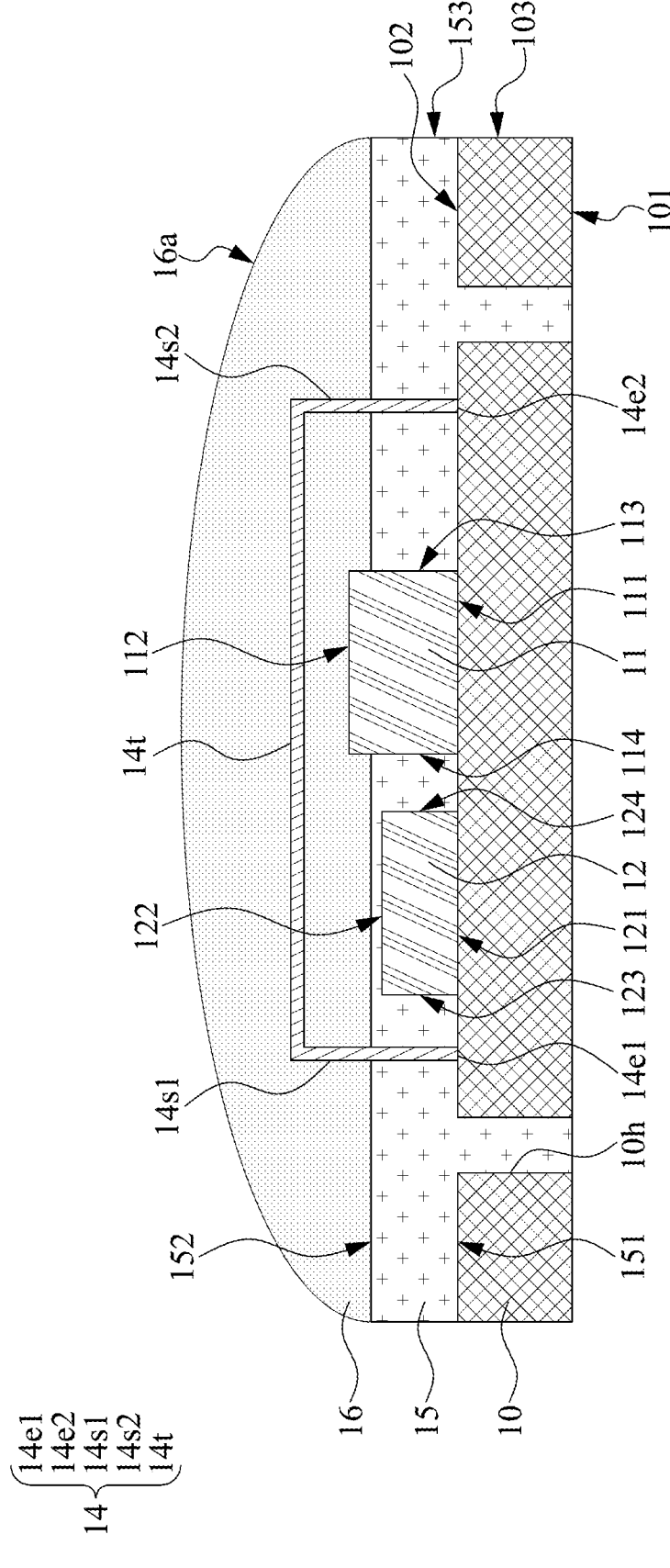

FIG. 1D-1 illustrates a perspective view of a sensing device 1d in accordance with some arrangements of the present disclosure. FIG. 1D-2 illustrates a cross-sectional view of the sensing device 1d in accordance with some arrangements of the present disclosure. The sensing device 1d is similar to the sensing device 1a in FIG. 1C except for the differences described as follows.

The flexible connection element 14 may include two straight (e.g., vertical) sides or walls 14s1 and 14s2 and a straight (e.g., horizontal) top or bridge 14t connecting between the two sides 14s1 and 14s2. The top 14t of the flexible connection element 14 may be parallel to the surface 101 and/or the surface 102 of the carrier 10. The top 14t of the flexible connection element 14 may extend over or across the electronic components 11 and 12. In some arrangements, a projection area of the flexible connection element 14 over the carrier 10 and a projection area of the electronic component 11 over the carrier 10 may be at least partially overlapped. In some arrangements, a projection area of the flexible connection element 14 over the carrier 10 and a projection area of the electronic component 12 over the carrier 10 may be at least partially overlapped.

The electronic component 11 may include a surface 111 facing the carrier 10, a surface 112 opposite to the surface 111, and lateral surfaces 113, 114 extending between the surface 111 and the surface 112. The surface 111 may include an active surface and the surface 112 may include a backside surface. The electronic component 12 may include a surface 121 facing the carrier 10, a surface 122 opposite to the surface 111, and lateral surfaces 123, 124 extending between the surface 121 and the surface 122. The surface 121 may include an active surface and the surface 122 may include a backside surface.

For example, the side 14s1 of the flexible connection element 14 may be disposed adjacent to the lateral surface 123 of the electronic component 12 and the top 14t of the flexible connection element 14 may extend over or across the surface 122 of the electronic component 12. In some arrangements, the side 14s1 of the flexible connection element 14 may extend along the lateral surface 123 of the electronic component 12. In some arrangements, the side 14s1 of the flexible connection element 14 may contact the lateral surface 123 of the electronic component 12.

For example, the side 14s2 of the flexible connection element 14 may be disposed adjacent to the lateral surface 113 of the electronic component 11 and the top 14t of the flexible connection element 14 may extend over or across the surface 112 of the electronic component 11. In some arrangements, the side 14s2 of the flexible connection element 14 may extend along the lateral surface 113 of the electronic component 11. In some arrangements, the side 14s2 of the flexible connection element 14 may contact the lateral surface 113 of the electronic component 11.

Figure 1E:
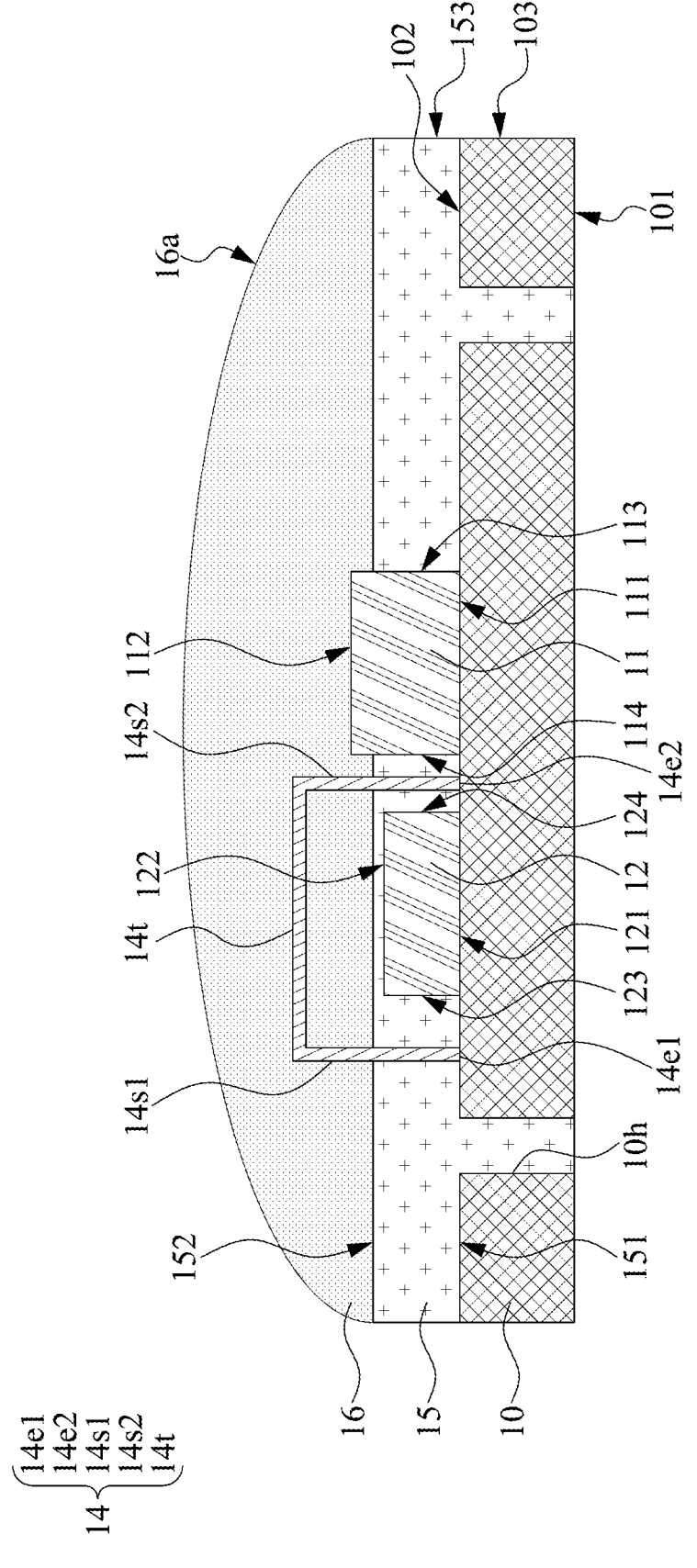
FIG. 1E illustrates a cross-sectional view of a sensing device in accordance with some arrangements of the present disclosure.

In some arrangements, the lateral surface 123 of the electronic component 12 and the lateral surface 113 of the electronic component 11 may physically support the flexible connection element 14 during a molding process (such as transfer molding process or compression molding process) for forming the encapsulant 15 and the encapsulant 16. Therefore, the risk of breaking the flexible connection element 14 is eliminated. FIG. 1E illustrates a cross-sectional view of a sensing device 1e in accordance with some arrangements of the present disclosure. The sensing device 1e is similar to the sensing device 1d in FIG. 1D-2 except for the differences described as follows.

The ends 14e1 and 14e2 of the flexible connection element 14 may be disposed over or on opposite lateral surfaces 123 and 124 of the electronic component 12. The side 14s1 of the flexible connection element 14 may be disposed adjacent to the lateral surface 123 of the electronic component 12 and the top 14t of the flexible connection element 14 may extend over or across the surface 122 of the electronic component 12. The side 14s2 of the flexible connection element 14 may extend between the electronic components 11 and 12. The side 14s2 of the flexible connection element 14 may be disposed between the electronic components 11 and 12.

In some arrangements, the lateral surfaces 123 and 124 of the electronic component 12 may physically support the flexible connection element 14 during a molding process (such as transfer molding process or compression molding process) for forming the encapsulant 15 and the encapsulant 16. Therefore, the risk of breaking the flexible connection element 14 is eliminated.

Figure 1F:
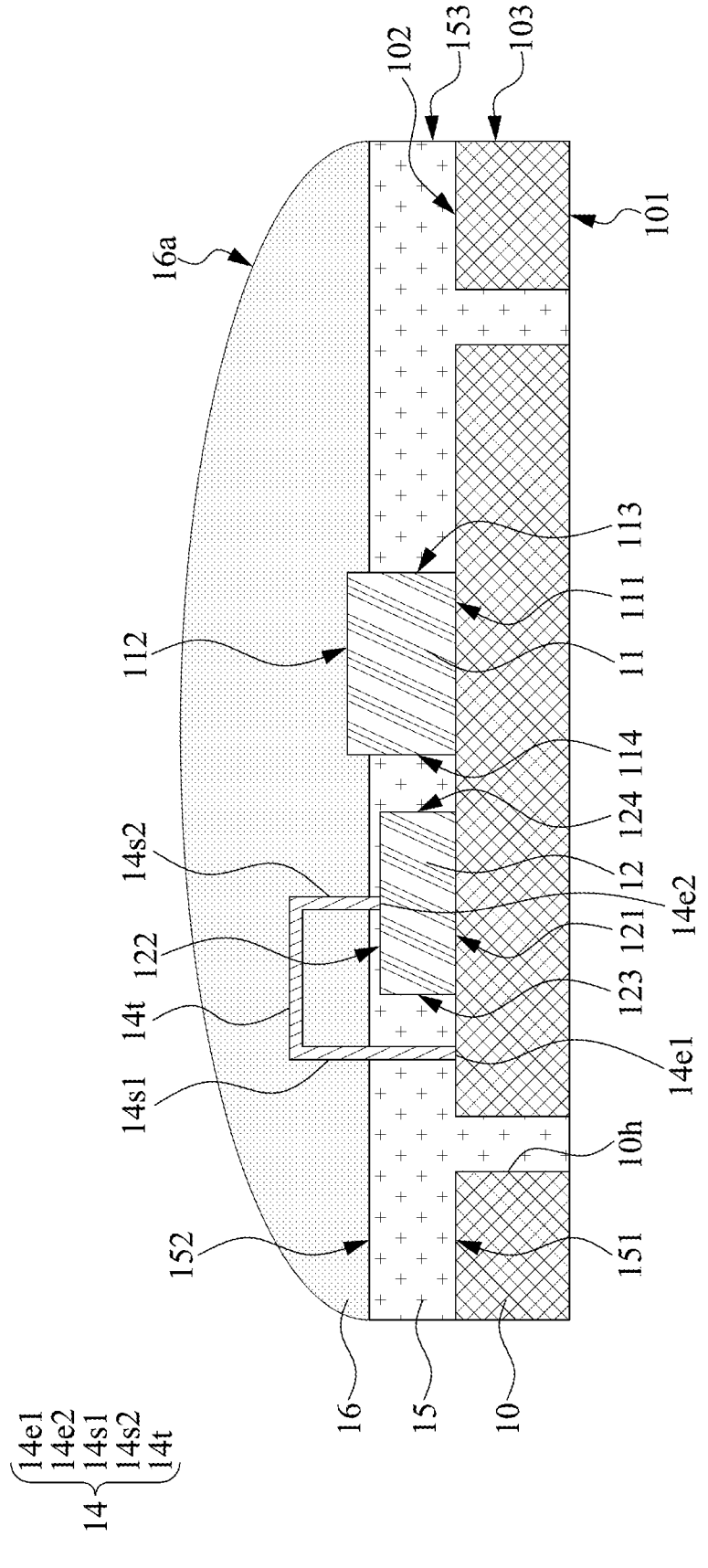
FIG. 1F illustrates a cross-sectional view of a sensing device in accordance with some arrangements of the present disclosure.

FIG. 1F illustrates a cross-sectional view of a sensing device 1f in accordance with some arrangements of the present disclosure. The sensing device 1f is similar to the sensing device 1e in FIG. 1E except for the differences described as follows.

The end 14e1 of the flexible connection element 14 may be disposed over or on the surface 102 of the carrier 10 and adjacent to the lateral surface 123 of the electronic component 12. The end 14e2 of the flexible connection element 14 may be disposed over or on the surface 122 of the electronic component 12. In some arrangements, the end 14e1 of the flexible connection element 14 may be fixed over or on the surface 102 of the carrier 10. The end 14e2 of the flexible connection element 14 may be fixed over or on the surface 122 of the electronic component 12.

In some arrangements, the surface 121 (which may be an active surface or a backside surface) of the electronic component 12 may be electrically connected with the encapsulant 16 through the side 14s1 of the flexible connection element 14 and the carrier 10.

In some arrangements, the surface 122 (which may be an active surface or a backside surface) of the electronic component 12 may be electrically connected with the encapsulant 16 through the side 14s2 of the flexible connection element 14. For example, a signal transmission path between the encapsulant 16 and the surface 122 of the electronic component 12 may be provided. The signals or pieces of information detected or collected by the encapsulant 16 may be transmitted to the surface 122 of the electronic component 12 through the side 14s2 of the flexible connection element 14 without passing through the carrier 10.

Figure 1G:
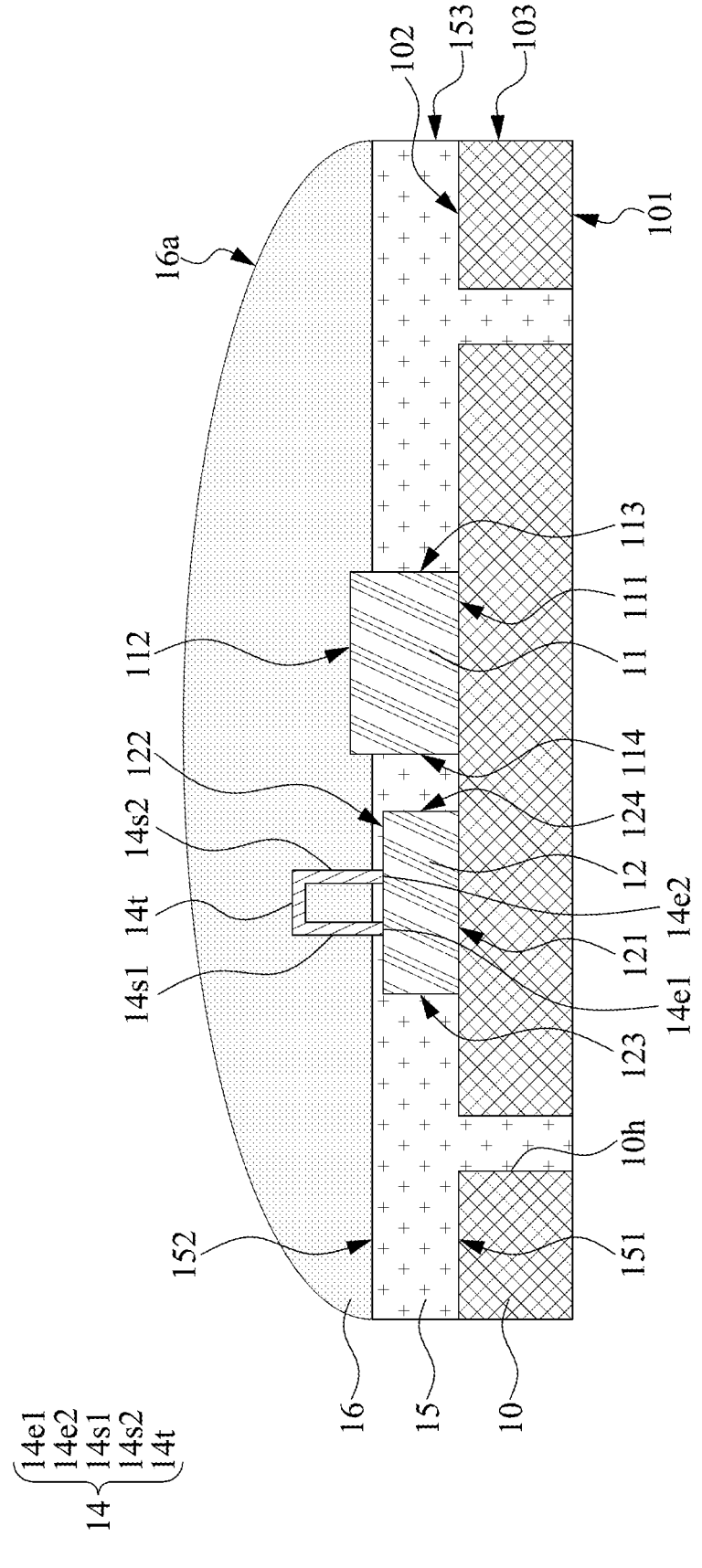
FIG. 1G illustrates a cross-sectional view of a sensing device in accordance with some arrangements of the present disclosure.

FIG. 1G illustrates a cross-sectional view of a sensing device 1g in accordance with some arrangements of the present disclosure. The sensing device 1g is similar to the sensing device 1f in FIG. 1F except for the differences described as follows.

The ends 14e1 and 14e2 of the flexible connection element 14 may be disposed over the surface 122 of the electronic component 12.

In some arrangements, the surface 122 (which may be an active surface or a backside surface) of the electronic component 12 may be electrically connected with the encapsulant 16 through the flexible connection element 14. For example, a signal transmission path between the encapsulant 16 and the surface 122 of the electronic component 12 may be provided. The signals or pieces of information detected or collected by the encapsulant 16 may be transmitted to the surface 122 of the electronic component 12 through the flexible connection element 14 without passing through the carrier 10.

Figure 1H:
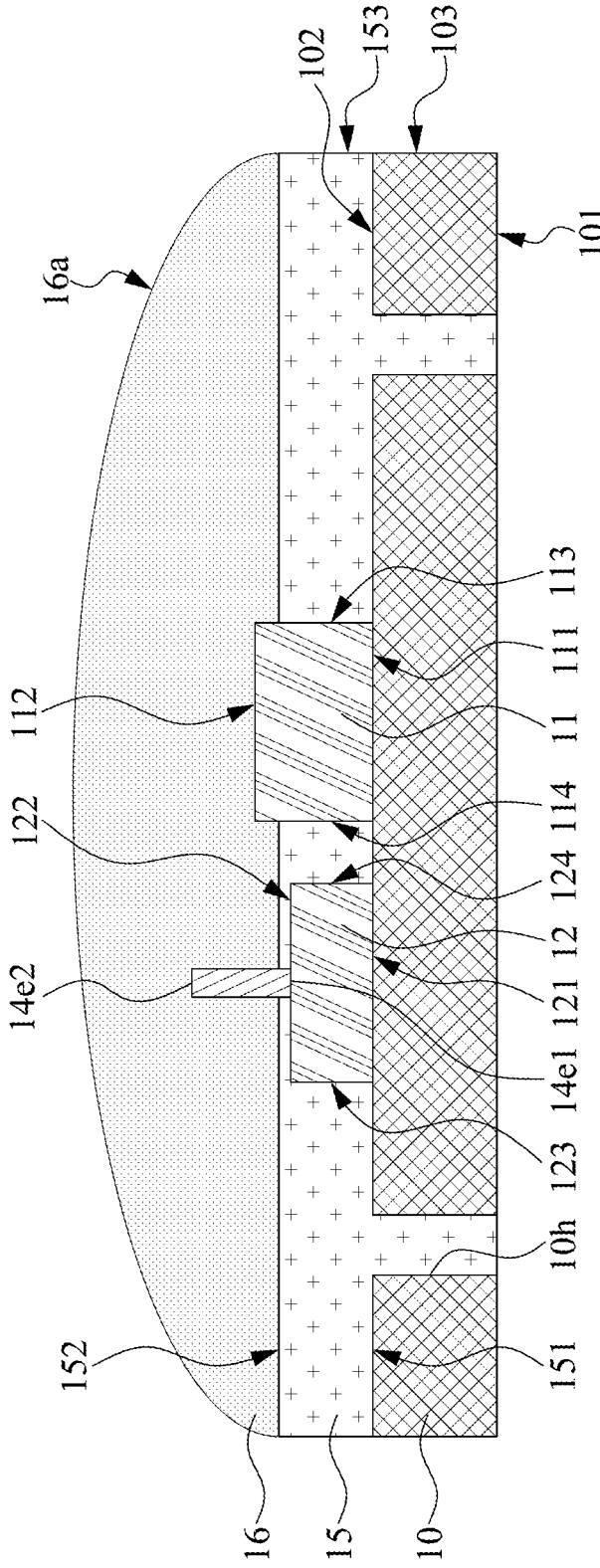
FIG. 1H illustrates a cross-sectional view of a sensing device in accordance with some arrangements of the present disclosure.

FIG. 1H illustrates a cross-sectional view of a sensing device 1h in accordance with some arrangements of the present disclosure. The sensing device 1h is similar to the sensing device 1g in FIG. 1G except for the differences described as follows.

The end 14e1 of the flexible connection element 14 may be disposed over the surface 122 of the electronic component 12 and the end 14e2 of the flexible connection element 14 may be covered or surrounded by the encapsulant 16.

Figures 1, 1I:
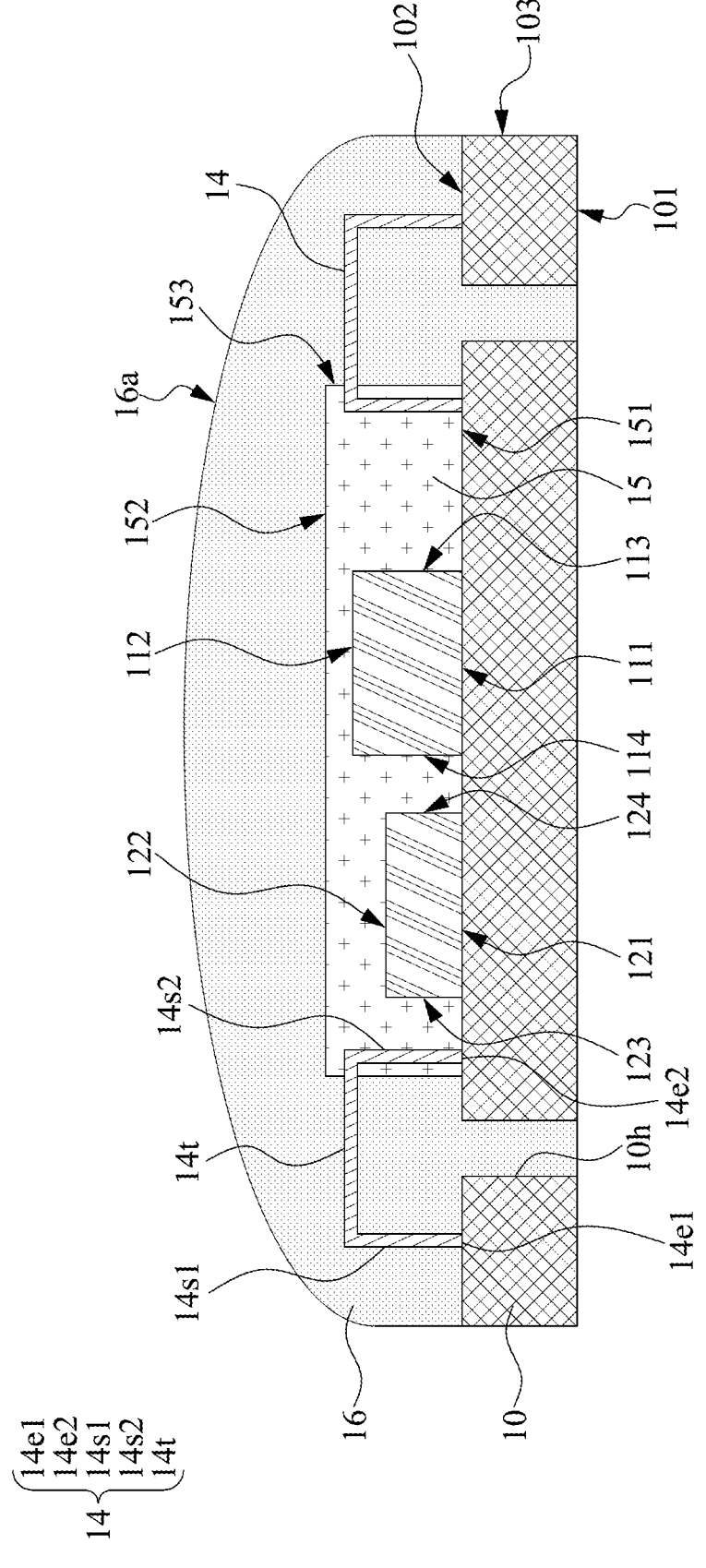
Figures 1, 1I, 2:
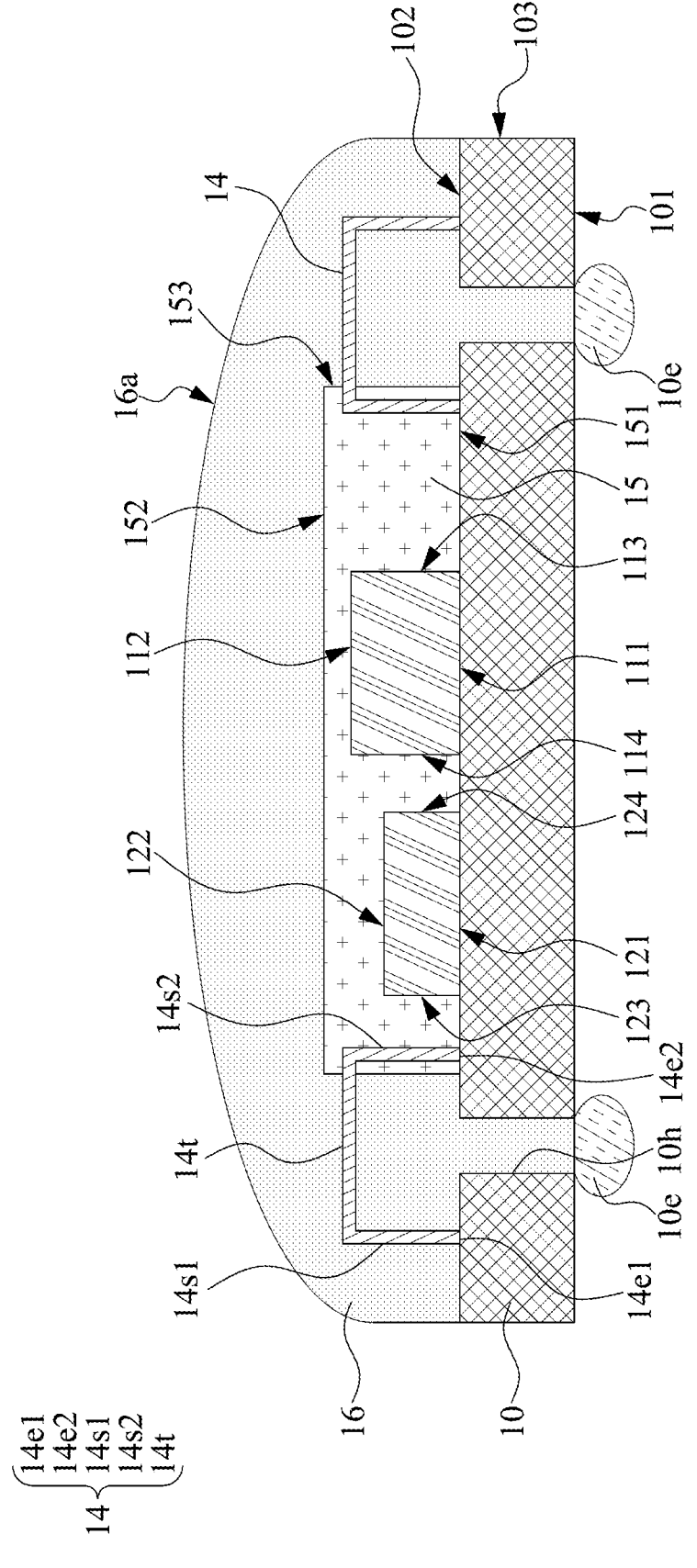

FIG. 1I-1 illustrates a cross-sectional view of a sensing device 1i in accordance with some arrangements of the present disclosure. The sensing device 1i is similar to the sensing device 1a in FIG. 1C except for the differences described as follows.

The encapsulant 15 may be covered, surrounded, or embedded by the encapsulant 16. The encapsulant 15 may be entirely covered, surrounded, or embedded by the encapsulant 16. In some arrangements, the projection area of the encapsulant 15 on the carrier 10 may be smaller than the projection area of the encapsulant 16 on the carrier 10. The surface 153 of the encapsulant 15 may not be coplanar or aligned with the surface 103 of the carrier 10. The surface 153 of the encapsulant 15 may be inside of the surface 103 of the carrier 10. The surface 153 of the encapsulant 15 may be covered by the encapsulant 16.

In some arrangements, the electronic components 11 and 12 may be covered, surrounded, or embedded by the encapsulant 15. The electronic components 11 and 12 may be spaced apart from the encapsulant 16 by the encapsulant 15.

In some arrangements, the end 14e1 and the side 14s1 of the flexible connection element 14 may be disposed in the encapsulant 16. The end 14e2 and the side 14s2 of the flexible connection element 14 may be disposed in the encapsulant 15. For example, the top 14t of the flexible connection element 14 may extend through the surface 153 of the encapsulant 15.

In some arrangements, the ends 14e1 and 14e2 of the flexible connection element 14 may both be disposed in the encapsulant 16. For example, the flexible connection element 14 may be separated from or spaced apart from the encapsulant 15. For example, the flexible connection element 14 may not contact the encapsulant 15. For example, the flexible connection element 14 may be entirely covered or surrounded by the encapsulant 16.

The holes 10h may be filled with the encapsulant 16. For example, the encapsulant 16 may be disposed over or on the surface 102 of the carrier 10 and extend into the holes 10h. For example, the encapsulant 16 may contact (such as directly contact) the sidewalls of the holes 10h. For example, the encapsulant 16 may be partially exposed from the surface 101 of the carrier 10. For example, the encapsulant 16 and the surface 101 of the carrier 10 may substantially coplanar.

In some arrangements, the carrier 10 and the encapsulant 16 may include different materials. The holes 10h and the encapsulant 16 may function as lock and key elements or interlocking mechanical features. The holes 10h may be configured to bond, connect, or lock the encapsulant 16 over or on the surface 102 of the carrier 10. Therefore, the adhesion force between the carrier 10 and the encapsulant 16 may be increased.

FIG. 1I-2 illustrates a cross-sectional view of a sensing device 1i' in accordance with some arrangements of the present disclosure. The sensing device 1i' in FIG. 1I-2 is similar to the sensing device 1i in FIG. 1I except that the sensing device 1i' in FIG. 1I-2 further comprises electrical contacts 10e disposed over the encapsulant 16 exposed by the surface 101 of the carrier 10.

In some arrangements, the electrical contacts 10e may include a solder ball, such as a controlled collapse chip connection (C4) bump, a ball grid array (BGA), a land grid array (LGA), and so on. In some arrangements, the electrical contacts 10e may include a conductive pad, a conductive via, a conductive pillar, a conductive wire, a board-to-board connector or a connector for HotBar soldering, or a combination thereof. In some arrangements, the electrical contacts 10e may be configured to provide electrical connections between the sensing device 1i' and external components (e.g., external circuits or circuit boards).

Figure 2A:
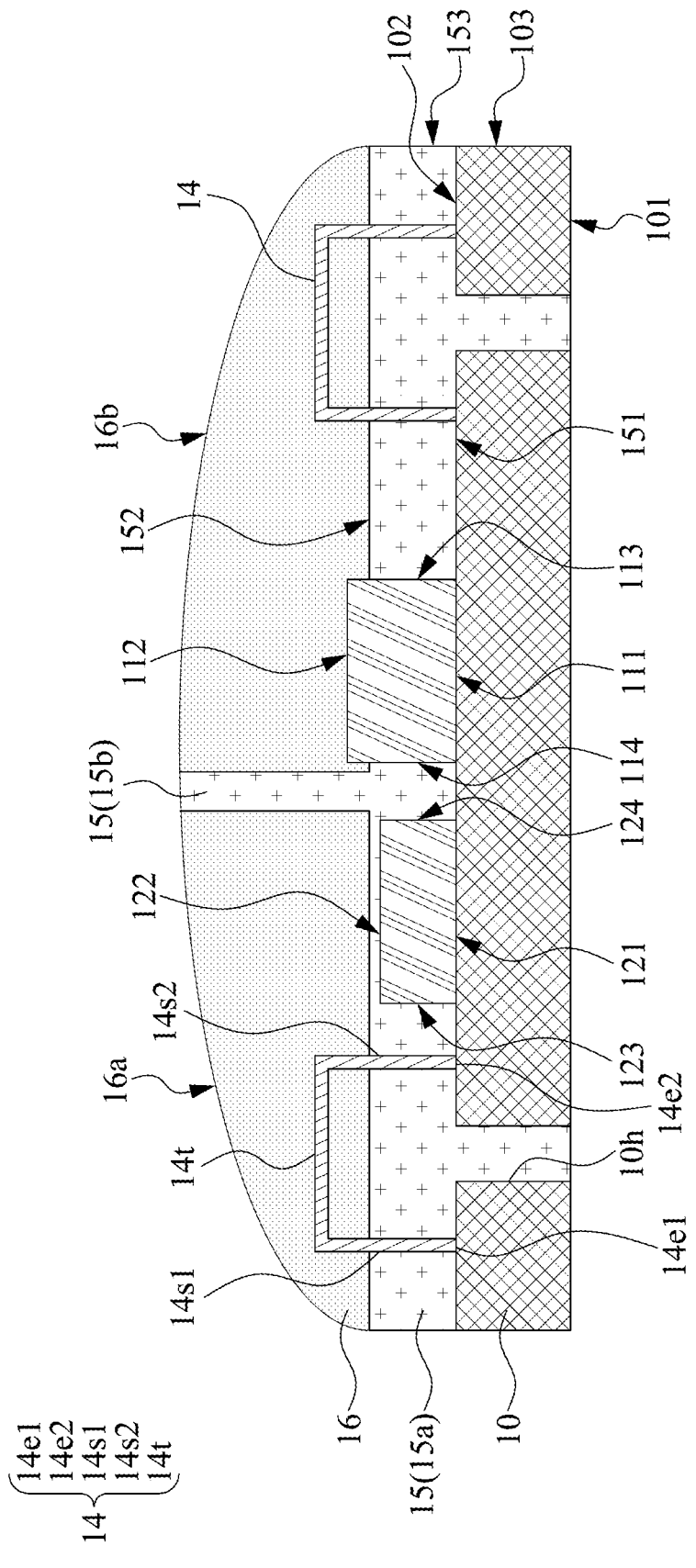
FIG. 2A illustrates a cross-sectional view of a sensing device in accordance with some arrangements of the present disclosure.

FIG. 2A illustrates a cross-sectional view of a sensing device 2a in accordance with some arrangements of the present disclosure. The sensing device 2a is similar to the sensing device 1a in FIG. 1C except for the differences described as follows.

The encapsulant 16 may include compartments, or separate sections or parts. The encapsulant 16 may include sensing areas 16a and 16b. The sensing areas 16a and 16b may be spaced apart from each other. The sensing areas 16a and 16b may be physically separated by the encapsulant 15. The sensing areas 16a and 16b may be isolated or insulated from each other by the encapsulant 15.

The sensing areas 16a and 16b may be configured to detect or collect different signals or pieces of information. For example, the sensing areas 16a and 16b may be configured to detect or collect signals having different electrical voltages. For example, the sensing area 16a may be configured to detect or collect signals having positive potentials and the sensing area 16b may be configured to detect or collect signals having negative potentials, or vice versa. For example, the sensing areas 16a and 16b may be configured to detect or collect signals carrying different biological or physiological information. The sensing areas 16a and 16b may each be electrically connected with the carrier 10 through one of the flexible connection elements 14.

The encapsulant 15 may include portions 15a and 15b. The portion 15a may be disposed over or on the surface 102 of the carrier 10 and the portion 15b may extend from the portion 15a. The portion 15b may protrude from the surface 152. The portion 15b may be disposed between the sensing areas 16a and 16b. The portion 15b and the sensing areas 16a and 16b may collaboratively form a curved surface.

Figure 2B:
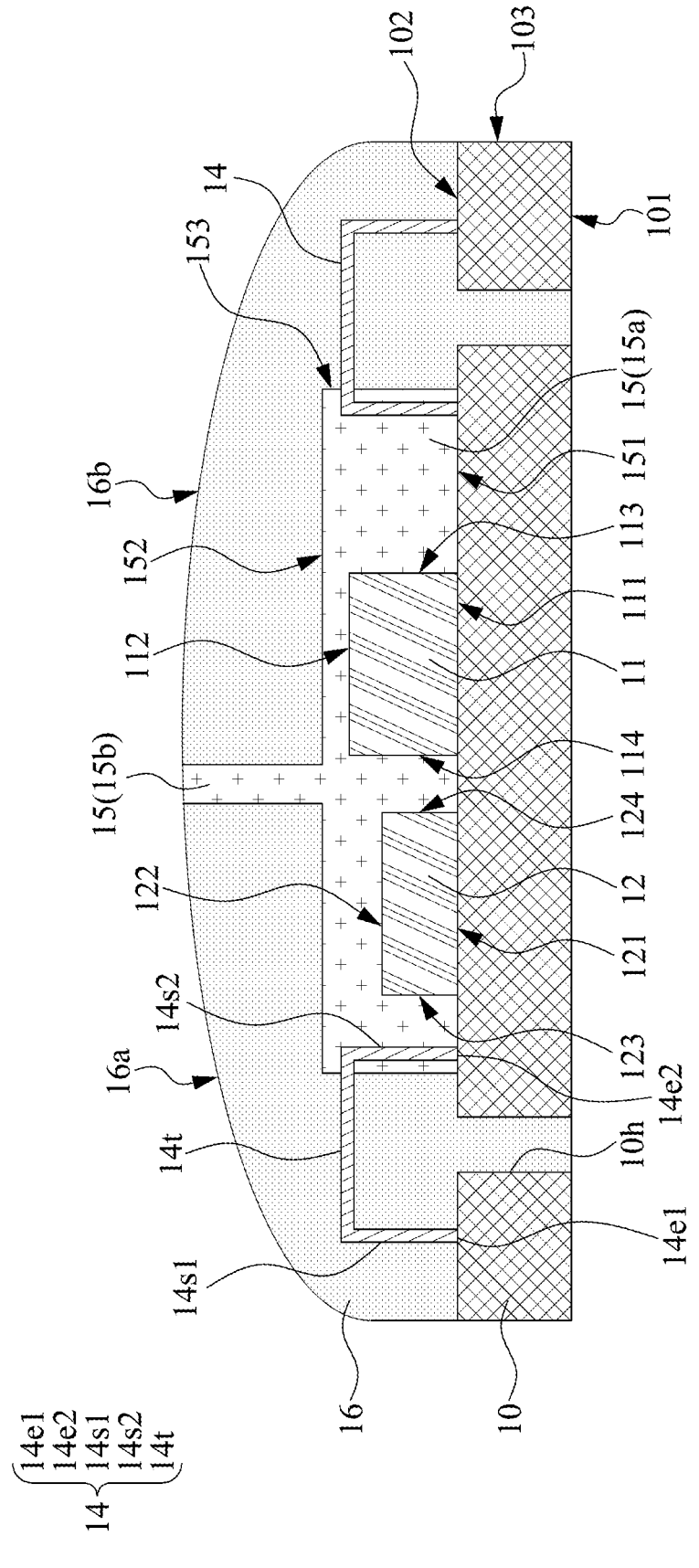
FIG. 2B illustrates a cross-sectional view of a sensing device in accordance with some arrangements of the present disclosure.

FIG. 2B illustrates a cross-sectional view of a sensing device 2b in accordance with some arrangements of the present disclosure. The sensing device 2b is similar to the sensing device 2a in FIG. 2A except for the differences described as follows.

The portion 15a of the encapsulant 15 may be covered, surrounded, or embedded by the encapsulant 16. In some arrangements, the projection area of the encapsulant 15 on the carrier 10 may be smaller than the projection area of the encapsulant 16 on the carrier 10. The surface 153 of the encapsulant 15 may not be coplanar or aligned with the surface 103 of the carrier 10. The surface 153 of the encapsulant 15 may be inside of the surface 103 of the carrier 10. The surface 153 of the encapsulant 15 may be covered by the encapsulant 16. The encapsulant 16 includes two portions separated by the encapsulant 15.

In some arrangements, the electronic components 11 and 12 may be covered, surrounded, or embedded by the encapsulant 15. The electronic components 11 and 12 may be spaced apart from the encapsulant 16 by the encapsulant 15.

In some arrangements, the end 14e1 and the side 14s1 of the flexible connection element 14 may be disposed in the encapsulant 16. The end 14e2 and the side 14s2 of the flexible connection element 14 may be disposed in the encapsulant 15. For example, the top 14t of the flexible connection element 14 may extend through the surface 153 of the encapsulant 15.

In some arrangements, the ends 14e1 and 14e2 of the flexible connection element 14 may both be disposed in the encapsulant 16. For example, the flexible connection element 14 may be separated from or spaced apart from the encapsulant 15. For example, the flexible connection element 14 may not contact the encapsulant 15. For example, the flexible connection element 14 may be entirely covered or surrounded by the encapsulant 16.

The holes 10h may be filled with the encapsulant 16. For example, the encapsulant 16 may be disposed over or on the surface 102 of the carrier 10 and extend into the holes 10h. For example, the encapsulant 16 may contact (such as directly contact) the sidewalls of the holes 10h. For example, the encapsulant 16 may be partially exposed from the surface 101 of the carrier 10. For example, the encapsulant 16 and the surface 101 of the carrier 10 may substantially coplanar.

In some arrangements, the carrier 10 and the encapsulant 16 may include different materials. The holes 10h and the encapsulant 16 may function as lock and key elements or interlocking mechanical features. The holes 10h may be configured to bond, connect, or lock the encapsulant 16 over or on the surface 102 of the carrier 10. Therefore, the adhesion force between the carrier 10 and the encapsulant 16 may be increased.

Figure 2C:
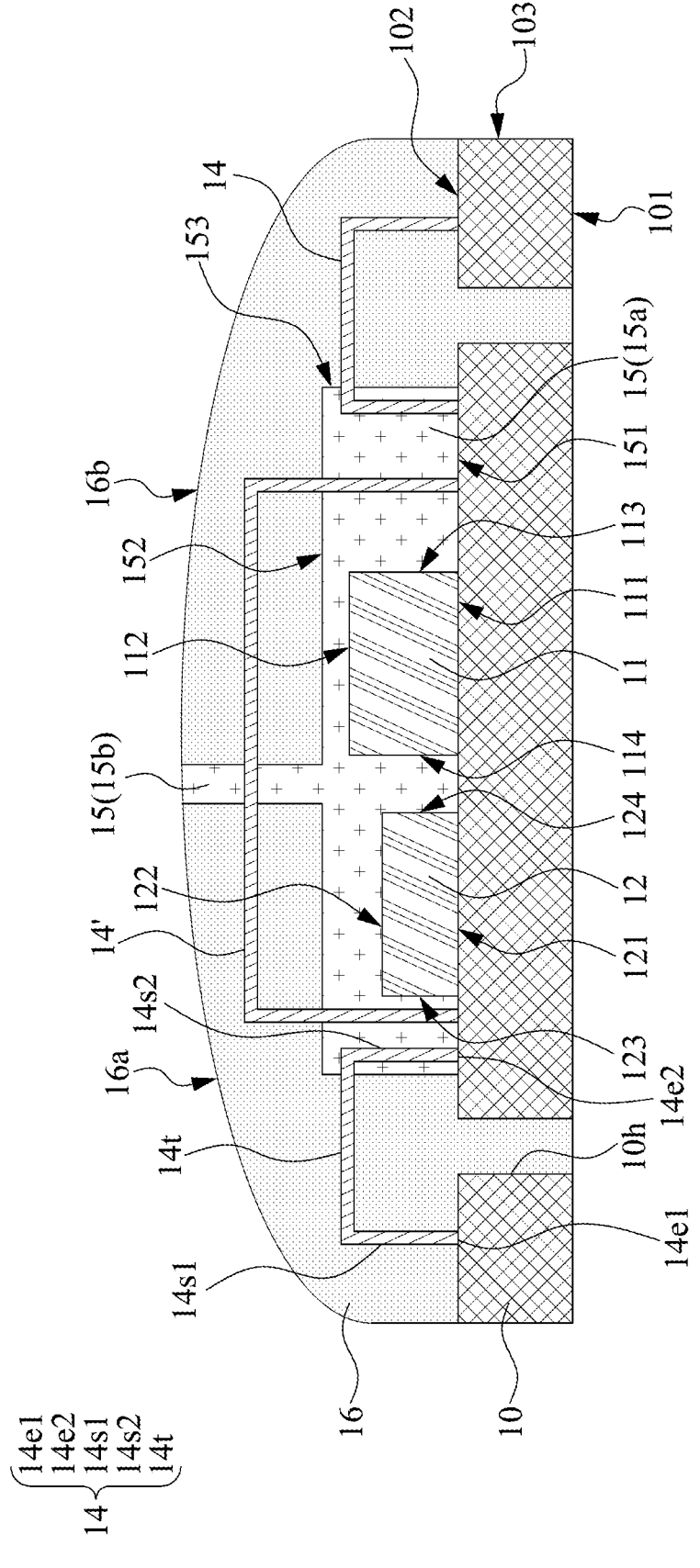
FIG. 2C illustrates a cross-sectional view of a sensing device in accordance with some arrangements of the present disclosure.

FIG. 2C illustrates a cross-sectional view of a sensing device 2c in accordance with some arrangements of the present disclosure. The sensing device 2c is similar to the sensing device 2b in FIG. 2B except that the sensing device 2c includes a flexible connection element 14' extending over the electronic components 11 and 12. The flexible connection element 14' may extend through the portion 15b and into the two portions of the encapsulant 16 separated by the encapsulant 15.

In some arrangements, the flexible connection element 14' may extend through a bonding interface between the encapsulant 16 and the encapsulant 15. In some arrangements, the flexible connection element 14' may extend through a bonding interface between the encapsulant 16 and the encapsulant 15 twice. In some arrangements, the encapsulant 16 and the encapsulant 15 may bonded with each other and may include different materials. The flexible connection element 14' may be configured to increase the adhesion force or bonding strength between the encapsulant 16 and the encapsulant 15.

Figure 3A:
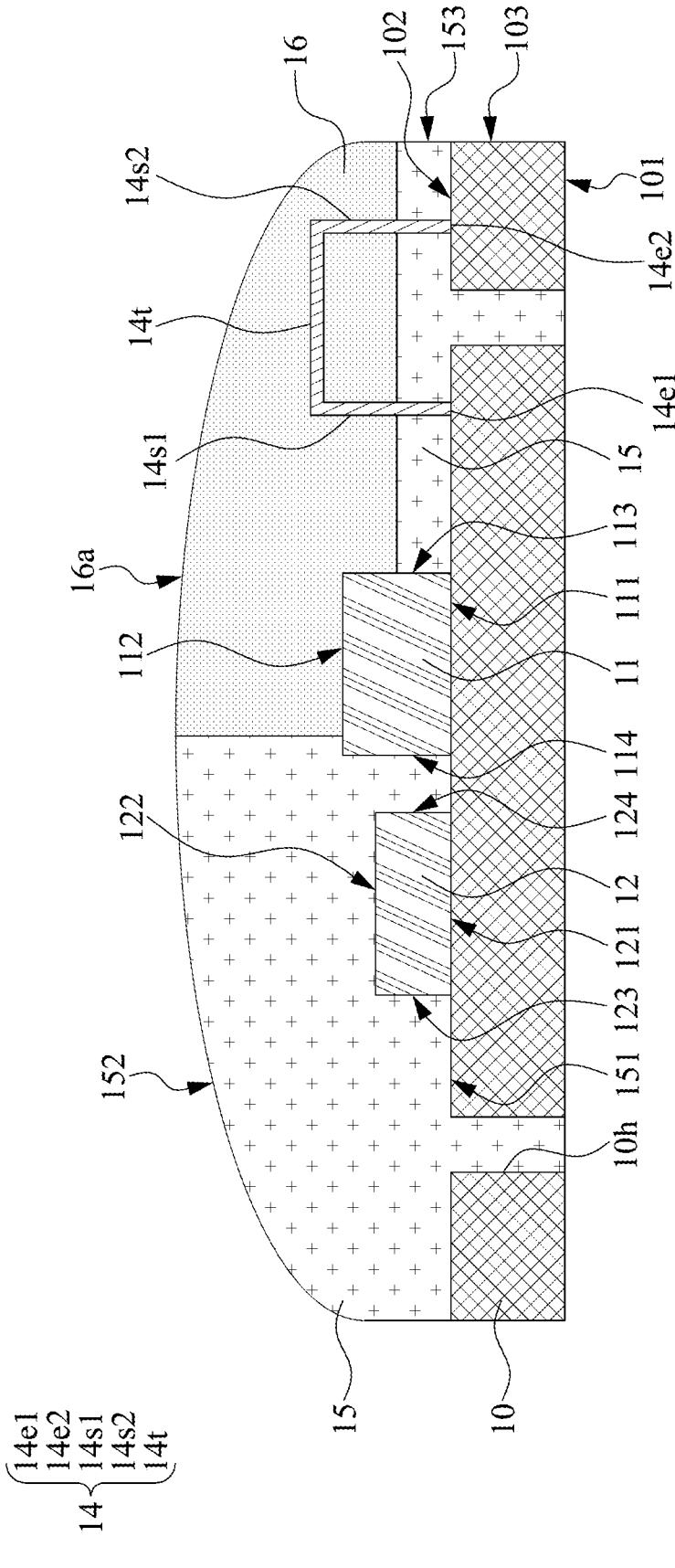
FIG. 3A illustrates a cross-sectional view of a sensing device in accordance with some arrangements of the present disclosure.

FIG. 3A illustrates a cross-sectional view of a sensing device 3a in accordance with some arrangements of the present disclosure. The sensing device 3a is similar to the sensing device 1a in FIG. 1C except for the differences described as follows.

The sensing area 16a of the encapsulant 16 may not extend across the surface area of the carrier 10. The sensing area 16a of the encapsulant 16 may cover or overlap about a half of the surface area of the carrier 10. In a direction substantially parallel to the surface 101 and/or the surface 102 of the carrier 10, the encapsulant 16 and the encapsulant 15 may be overlapped. In a direction substantially perpendicular to the surface 101 and/or the surface 102 of the carrier 10, the encapsulant 16 and the encapsulant 15 may be overlapped.

The encapsulant 15 may extend across the surface area of the carrier 10. The encapsulant 15 may have different thicknesses. A part of the encapsulant 15 may be covered by the encapsulant 16 and a part of the encapsulant 15 may be exposed from the encapsulant 16.

The surface 112 of the electronic component 11 may be covered by the encapsulant 16 and the encapsulant 15. However, in some other arrangements, the surface 112 of the electronic component 11 may be entirely covered by the encapsulant 16.

The surface 152 of the encapsulant 15 and the sensing area 16a of the encapsulant 16 may collaboratively form a curved surface. In some arrangements, the sensing area 16a of the encapsulant 16 may be configured to directly contact an object to be monitored or detected. In some arrangements, the surface 152 of the encapsulant 15 may be configured to isolate or insulate the sensing area 16a of the encapsulant 16 from directly contacting a metallic or conductive portion (e.g., a metallic strap) of a wearable device.

Therefore, the encapsulant 15 may help reducing signal interference, and the sensing quality can be improved.

Figure 3B:
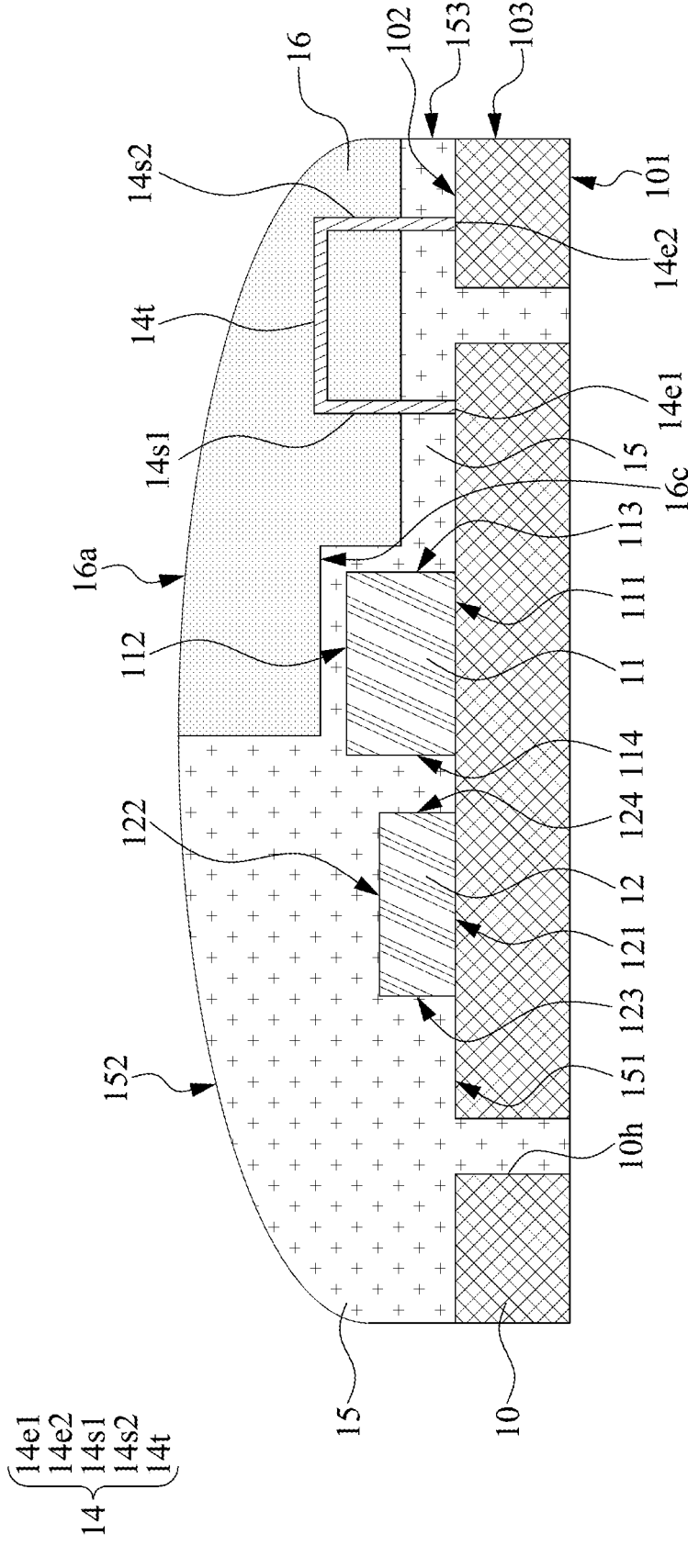
FIG. 3B illustrates a cross-sectional view of a sensing device in accordance with some arrangements of the present disclosure.

In some arrangements, the flexible connection element 14 may extend through a bonding interface between the encapsulant 16 and the encapsulant 15. In some arrangements, the flexible connection element 14 may extend through a bonding interface between the encapsulant 16 and the encapsulant 15 twice. In some arrangements, the encapsulant 16 and the encapsulant 15 may include different materials. The flexible connection element 14 may be configured to increase the adhesion force or bonding strength between the encapsulant 16 and the encapsulant 15. FIG. 3B illustrates a cross-sectional view of a sensing device 3b in accordance with some arrangements of the present disclosure. The sensing device 3b is similar to the sensing device 3a in FIG. 3A except for the differences described as follows.

The encapsulant 16 may have a stepped structure. The encapsulant 16 may have a corner or a cavity 16c facing and spaced apart from the electronic component 11. The corner 16c may be configured to accommodate the electronic component 11. The surface 112 of the electronic component 11 may be covered by the encapsulant 15.

The corner 16c may be filled with the encapsulant 15. The corner 16c and the encapsulant 15 may function as lock and key elements or interlocking mechanical features. The corner 16c may be configured to bond, connect, or lock the encapsulant 15. Therefore, the adhesion force between the encapsulant 16 and the encapsulant 15 may be increased.

Figure 4A:
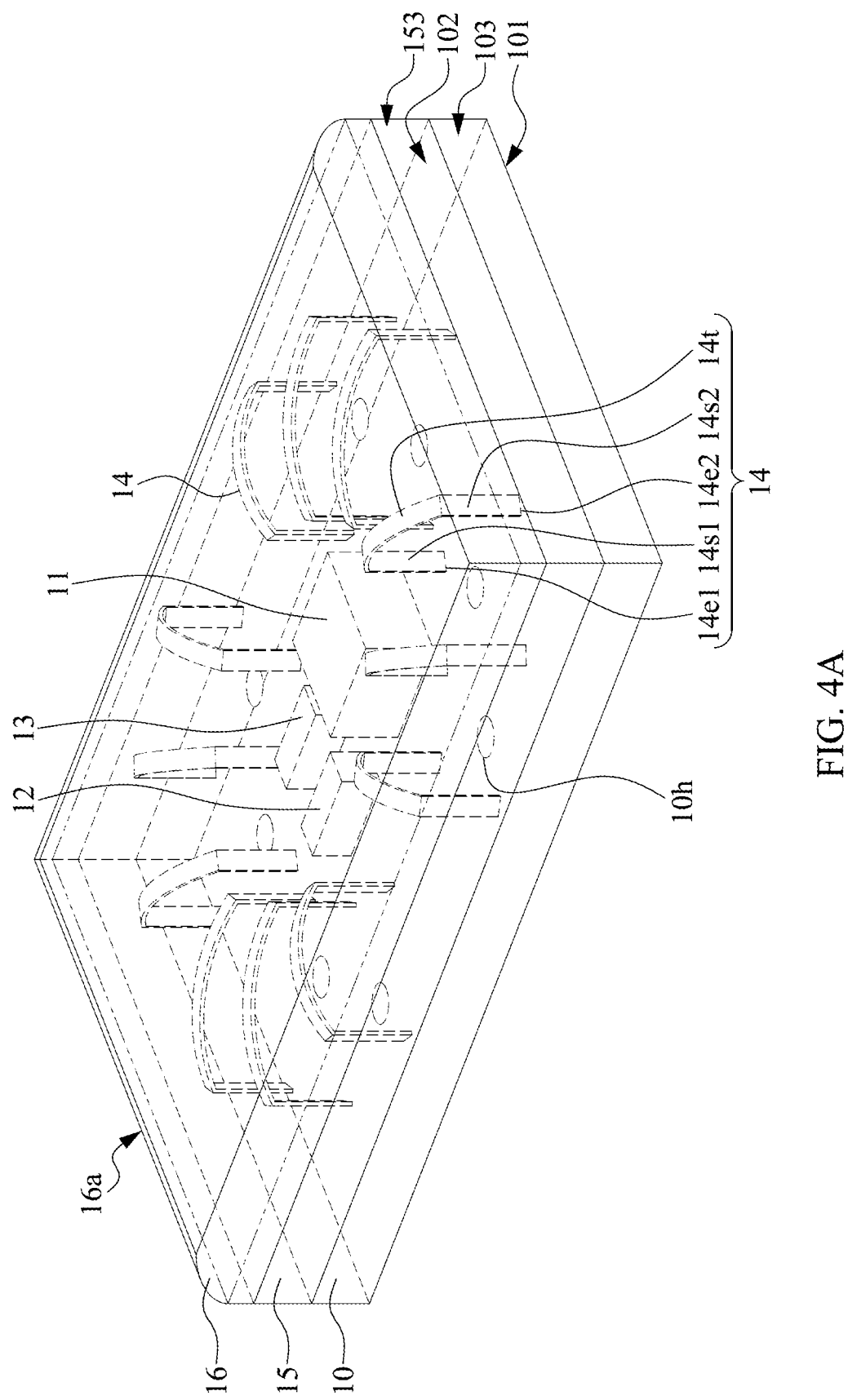
FIG. 4A illustrates a perspective view of a sensing device in accordance with some arrangements of the present disclosure.
Figure 4B:
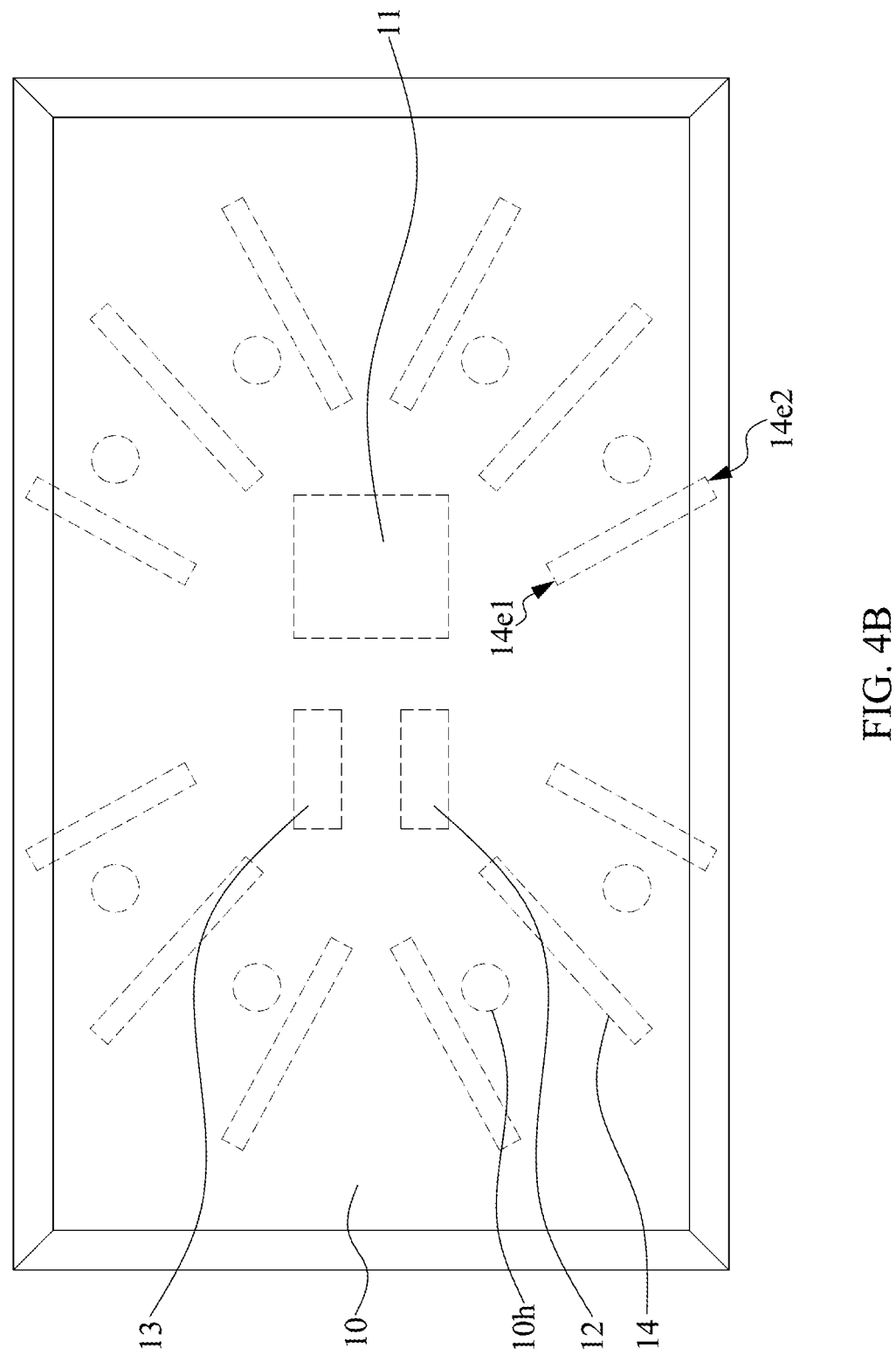
FIG. 4B illustrates a top view of a sensing device in accordance with some arrangements of the present disclosure.
Figure 4C:
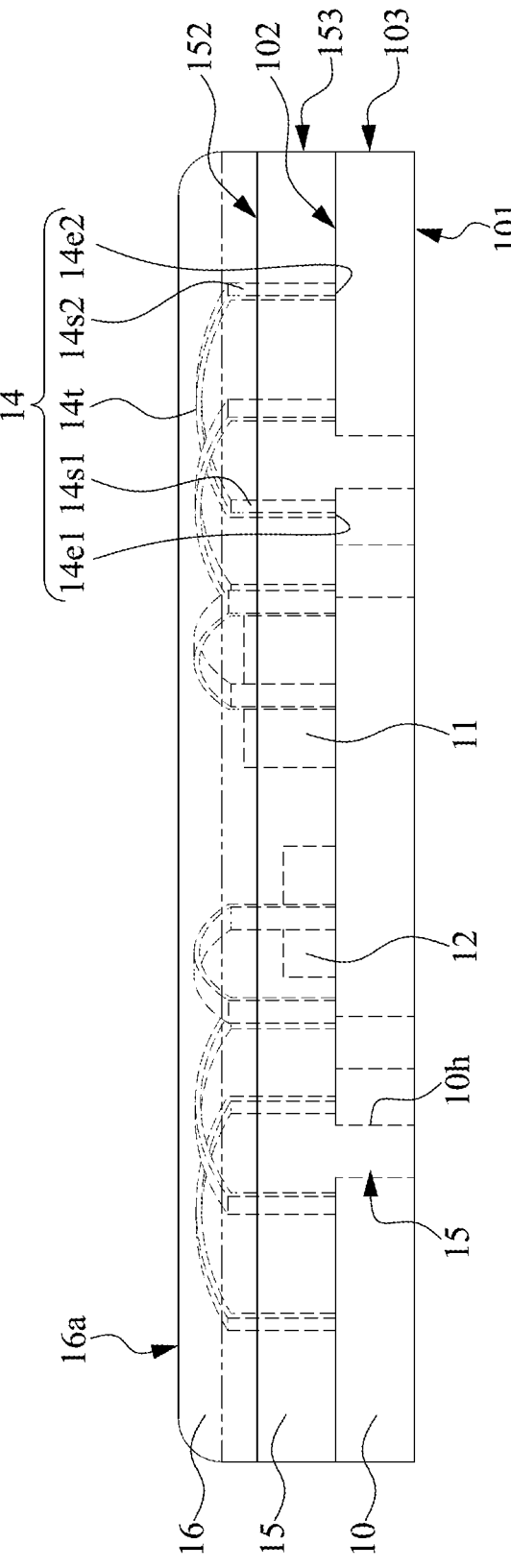
FIG. 4C illustrates a side view of a sensing device in accordance with some arrangements of the present disclosure.

FIG. 4A illustrates a perspective view of a sensing device 4a in accordance with some arrangements of the present disclosure. FIG. 4B and FIG. 4C illustrate a top view and a side view, respectively, of the sensing device 4a in accordance with some arrangements of the present disclosure. The sensing device 4a is similar to the sensing device 4a in FIGS. 1A, 1B, and 1C except that the sensing device 4a has a rectangular shape from the top view. The shape of the sensing device is not intended to limit the present disclosure. For example, the sensing device may be circular, oval, triangular, or other shapes.

Figure 5:
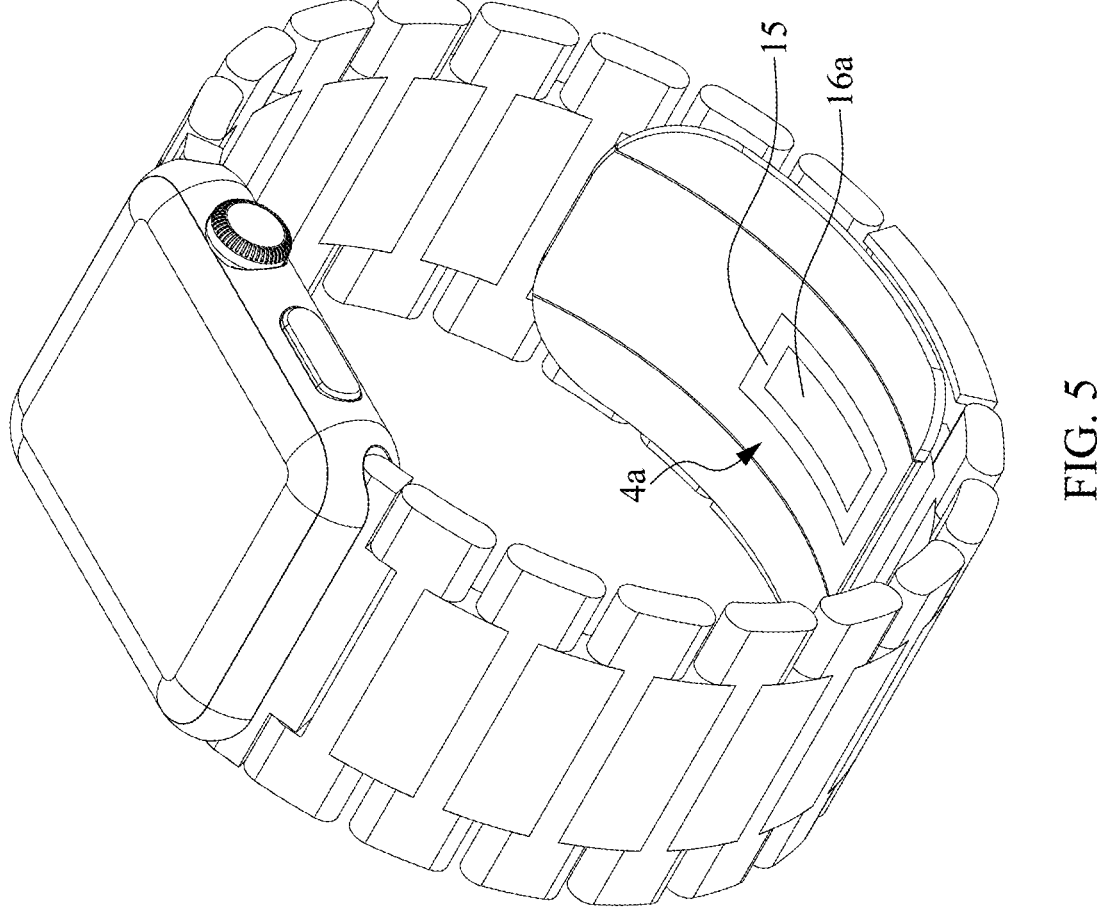
FIG. 5 illustrates a perspective view of a wearable device in accordance with some arrangements of the present disclosure.

FIG. 5 illustrates a perspective view of a wearable device 5 in accordance with some arrangements of the present disclosure.

The sensing device 4a may be incorporated in the wearable device 5. In some arrangements, the sensing device 4a may be secured or fixed to an opening of the wearable device 5. For example, the sensing device 4a may be mechanically joined or connected to the opening of the wearable device 5.

For example, the sensing device 4a and the opening of the wearable device 5 may have a mechanical or magnetic means to resist or arrest the movement of the sensing device 4a. The mechanical or magnetic means may prevent unintended separation of the sensing device 4a and the opening of the wearable device 5. The mechanical or magnetic means may include locking elements, fastening elements, retaining elements, etc. More specifically, the mechanical or magnetic means may include a pin, a post, a spring, a plugger, a buffer, a snap, a clip, a contour, etc.

In some arrangements, the sensing device 4a may be configured to constructively form a part of the wearable device 5. In some arrangements, the sensing device 4a may be attached, removed, and reattached to the wearable device 5. In some arrangements, the sensing device 4a may be configured to provide or support auxiliary or supplementary function or operation of the wearable device 5. The wearable device 5 may be configured to be worn by and/or attached to an object (or a wearing object) or a target. The wearable device 5 may be configured to connect the sensing area 16a of the sensing device 4a to the object. The wearable device 5 may be configured to bring the sensing area 16a of the sensing device 4a to be closer to the object. The wearable device 5 may be configured to keep or define a distance between the sensing area 16a of the sensing device 4a and the object. In some arrangements, an outer surface of the sensing device 4a may be conformal to a wearing surface of a structure (such as a frame, a housing, a supporting or an accessory part) of the wearable device 5 accommodating the sensing device 4a.

Furthermore, the shape or dimension of the sensing device 4a can be adjusted to adapt to the wearable device 5. For example, if the wearable device 5 has a metallic strap, the sensing area 16a of the encapsulant 16 (in FIG. 4C) may be covered or surrounded by the encapsulant 15 and separated from the metallic strap by the encapsulant 15. For example, in the side view in FIG. 4C, the surface 103 of the carrier 10 may be at least partially covered or surrounded by the encapsulant 15. Therefore, the encapsulant 15 may help reducing signal interference, and the sensing quality can be improved.

As used herein, the singular terms "a," "an," and "the" may include a plurality of referents unless the context clearly dictates otherwise.

As used herein, the terms "conductive," "electrically conductive" and "electrical conductivity" refer to an ability to transport an electric current. Electrically conductive materials typically indicate those materials that exhibit little or no opposition to the flow of an electric current. One measure of electrical conductivity is Siemens per meter (S/m). Typically, an electrically conductive material is one having a conductivity greater than approximately $10^4$ S/m, such as at least $10^5$ S/m or at least $10^6$ S/m. The electrical conductivity of a material can sometimes vary with temperature. Unless otherwise specified, the electrical conductivity of a material is measured at room temperature.

As used herein, the terms "approximately," "substantially," "substantial" and "about" are used to describe and account for small variations. When used in conjunction with an event or circumstance, the terms can refer to instances in which the event or circumstance occurs precisely as well as instances in which the event or circumstance occurs to a close approximation. For example, when used in conjunction with a numerical value, the terms can refer to a range of variation of less than or equal to ±10% of that numerical value, such as less than or equal to ±5%, less than or equal to ±4%, less than or equal to ±3%, less than or equal to ±2%, less than or equal to ±1%, less than or equal to ±0.5%, less than or equal to ±0.1%, or less than or equal to ±0.05%. For example, two numerical values can be deemed to be "substantially" the same or equal if a difference between the values is less than or equal to ±10% of an average of the values, such as less than or equal to ±5%, less than or equal to ±4%, less than or equal to ±3%, less than or equal to ±2%, less than or equal to ±1%, less than or equal to ±0.5%, less than or equal to ±0.1%, or less than or equal to ±0.05%. For example, "substantially" parallel can refer to a range of angular variation relative to 0° that is less than or equal to ±10°, such as less than or equal to ±5°, less than or equal to ±4°, less than or equal to ±3°, less than or equal to ±2°, less than or equal to ±1°, less than or equal to ±0.5°, less than or equal to ±0.1°, or less than or equal to ±0.05°. For example, "substantially" perpendicular can refer to a range of angular variation relative to 90° that is less than or equal to ±10°, such as less than or equal to ±5°, less than or equal to ±4°, less than or equal to ±3°, less than or equal to ±2°, less than or equal to ±1°, less than or equal to ±0.5°, less than or equal to ±0.1°, or less than or equal to =0.05°.

Additionally, amounts, ratios, and other numerical values are sometimes presented herein in a range format. It is to be understood that such range format is used for convenience and brevity and should be understood flexibly to include numerical values explicitly specified as limits of a range, but also to include all individual numerical values or sub-ranges encompassed within that range as if each numerical value and sub-range is explicitly specified.

While the present disclosure has been described and illustrated with reference to specific arrangements thereof, these descriptions and illustrations do not limit the present disclosure. It should be understood by those skilled in the art that various changes may be made and equivalents may be substituted without departing from the true spirit and scope of the present disclosure as defined by the appended claims. The illustrations may not be necessarily drawn to scale. There may be distinctions between the artistic renditions in the present disclosure and the actual apparatus due to manufacturing processes and tolerances. There may be other arrangements of the present disclosure which are not specifically illustrated. The specification and drawings are to be regarded as illustrative rather than restrictive. Modifications may be made to adapt a particular situation, material, composition of matter, method, or process to the objective, spirit and scope of the present disclosure. All such modifications are intended to be within the scope of the claims appended hereto. While the methods disclosed herein have been described with reference to particular operations performed in a particular order, it will be understood that these operations may be combined, sub-divided, or re-ordered to form an equivalent method without departing from the teachings of the present disclosure. Accordingly, unless specifically indicated herein, the order and grouping of the operations are not limitations of the present disclosure.

What is claimed is:

1. A sensing device, comprising:
   a carrier;
   a first processor disposed over a first surface of the carrier and electrically connected with the carrier;
   an encapsulant disposed over the carrier and covering the first processor;
   an electrode disposed over the encapsulant and configured to detect a signal external to the sensing device, wherein a projection area of the electrode on the carrier is substantially equal to a projection area of the encapsulant on the carrier; and
   a plurality of flexible connectors form a radial pattern and diverge from the first processor from a top view, wherein each flexible connector of the plurality of flexible connectors includes two straight sides perpendicular to the first surface of the carrier, and a curved top connecting between the two straight sides, and wherein the curved tops of the plurality of flexible connectors are covered by the electrode;
   wherein the plurality of flexible connectors are configured to receive the signal from the electrode and transmit the signal to the carrier and further to the first processor.

2. The sensing device of claim 1, wherein an impedance of the plurality of flexible connectors is lower than an impedance of the electrode.

3. The sensing device of claim 1, wherein carrier includes a second surface opposite to the first surface of the carrier and a plurality of holes extending between the first surface and the second surface.

4. The sensing device of claim 3, wherein the plurality of holes form a circle from the top view.

5. The sensing device of claim 3, wherein the plurality of holes are equally spaced from the top view.

6. The sensing device of claim 3, wherein the encapsulant extends into the plurality of holes.

7. The sensing device of claim 1, wherein a backside surface of the first processor is covered by the electrode.

8. The sensing device of claim 7, wherein the plurality of flexible connectors are partially covered by the electrode.

9. The sensing device of claim 1, wherein two ends of each flexible connector of the plurality of flexible connectors directly contact the carrier.

10. The sensing device of claim 9, wherein the curved tops are farthest portions of the plurality of flexible connectors from the carrier.

11. The sensing device of claim 1, further comprising:
a second processor disposed over a central portion of the first surface of the carrier.

12. The sensing device of claim 11, wherein an active surface of the second processor faces away from the carrier and is covered by the encapsulant.

13. The sensing device of claim 12, wherein a backside surface of the first processor faces away from the carrier and is covered by the electrode.

14. The sensing device of claim 12, further comprising:
a first flexible connector having two ends fixed over the first surface of the carrier, wherein the first flexible connector extends across the active surface of the second processor.

15. The sensing device of claim 12, wherein the further comprising:
a second flexible connector having an end fixed over the carrier and another end fixed over the active surface of the second processor.

16. The sensing device of claim 15, a farthest point of the second flexible connector from the carrier is covered by the electrode.

17. The sensing device of claim 12, further comprising:
a third flexible connector having two ends fixed over the active surface of the second processor.

18. The sensing device of claim 17, wherein the signal from the electrode is transmitted to the second processor through the third flexible connector without passing through the carrier.

19. The sensing device of claim 1, wherein a lateral surface of the encapsulant is substantially aligned with a lateral surface of the carrier.

20. The sensing device of claim 1, wherein the plurality of flexible connectors extend through a bonding interface between the encapsulant and the electrode.

* * * * *